United States Patent
Kubiak et al.

(10) Patent No.: US 11,547,397 B2
(45) Date of Patent: *Jan. 10, 2023

(54) DEVICES, SYSTEMS, AND METHODS FOR REPAIRING SOFT TISSUE AND ATTACHING SOFT TISSUE TO BONE

(71) Applicant: CONEXTIONS, INC., Salt Lake City, UT (US)

(72) Inventors: Erik N. Kubiak, Las Vegas, NV (US); Barrett J. Yates, Layton, UT (US); Roy M. Taylor, Salt Lake City, UT (US); Zackery K. Evans, Woods Cross, UT (US); Daniel K. Smith, Woods Cross, UT (US); Daniel L. Gruppo, Loveland, OH (US); Roy W. Sanders, Tampa, FL (US); Matthew J. Swift, Cottonwood Heights, UT (US)

(73) Assignee: CONEXTIONS, INC., Salt Lake City, UT (US)

( * ) Notice: Subject to any disclaimer, the term of this patent is extended or adjusted under 35 U.S.C. 154(b) by 372 days.

This patent is subject to a terminal disclaimer.

(21) Appl. No.: 16/287,414

(22) Filed: Feb. 27, 2019

(65) Prior Publication Data

US 2019/0261973 A1    Aug. 29, 2019

Related U.S. Application Data

(63) Continuation-in-part of application No. 16/279,337, filed on Feb. 19, 2019, now Pat. No. 10,973,509,
(Continued)

(51) Int. Cl.
*A61B 17/04* (2006.01)
*A61B 17/064* (2006.01)

(52) U.S. Cl.
CPC ...... *A61B 17/0401* (2013.01); *A61B 17/0482* (2013.01); *A61B 2017/0403* (2013.01);
(Continued)

(58) Field of Classification Search
None
See application file for complete search history.

(56) References Cited

U.S. PATENT DOCUMENTS

| 3,166,072 A | 1/1965 | Sullivan et al. |
| 4,388,926 A | 6/1983 | Shalaby et al. |

(Continued)

FOREIGN PATENT DOCUMENTS

| WO | WO2016061530 | 4/2016 |
| WO | WO2016138033 | 9/2016 |

OTHER PUBLICATIONS

Office Action with English Translation issued in CN 201580066314.4 dated Jun. 22, 2018.
(Continued)

*Primary Examiner* — Shaun L David
(74) *Attorney, Agent, or Firm* — David L. Stott

(57) ABSTRACT

Devices, systems and/or methods for fixating soft tissue to bone are provided. In one embodiment, a repair device for fixating soft tissue to bone with a bone anchor includes a soft tissue anchor and one or more flexible members. The soft tissue anchor includes a base with multiple legs extending from the base. The one or more flexible members are coupled to the base and configured to extend from the base to the bone anchor with a fixed length. With this arrangement, the fixed length of the one or more flexible members is configured to maintain a fixed distance between the soft tissue anchor and the bone anchor such that, as the bone anchor is seated into bone, the one or more flexible members
(Continued)

pulls the soft tissue anchor down against the soft tissue to fixate the soft tissue to the bone.

14 Claims, 17 Drawing Sheets

Related U.S. Application Data which is a continuation-in-part of application No. 16/226,573, filed on Dec. 19, 2018.

(60) Provisional application No. 62/633,000, filed on Feb. 20, 2018, provisional application No. 62/608,533, filed on Dec. 20, 2017.

(52) U.S. Cl.
CPC . *A61B 2017/044* (2013.01); *A61B 2017/0409* (2013.01); *A61B 2017/0412* (2013.01); *A61B 2017/0414* (2013.01); *A61B 2017/0437* (2013.01); *A61B 2017/0445* (2013.01); *A61B 2017/0448* (2013.01); *A61B 2017/0459* (2013.01); *A61B 2017/0464* (2013.01); *A61B 2017/0496* (2013.01); *A61B 2017/0641* (2013.01)

(56) References Cited

U.S. PATENT DOCUMENTS

| | | |
|---|---|---|
| 4,414,967 A | 11/1983 | Shapiro |
| 4,454,875 A | 6/1984 | Pratt et al. |
| 4,461,298 A | 7/1984 | Shalaby et al. |
| 4,469,101 A | 9/1984 | Coleman et al. |
| 4,489,875 A | 12/1984 | Crawford et al. |
| 4,532,926 A | 8/1985 | O'Holla |
| 4,534,350 A | 8/1985 | Golden et al. |
| 4,548,202 A | 10/1985 | Duncan |
| 4,610,250 A | 9/1986 | Green |
| 4,655,222 A | 4/1987 | Florez et al. |
| 4,655,980 A | 4/1987 | Chu |
| 4,741,330 A | 5/1988 | Hayhurst |
| 4,776,890 A | 10/1988 | Chu |
| 4,796,612 A | 1/1989 | Reese |
| 4,810,549 A | 3/1989 | Abrams et al. |
| 4,873,976 A | 10/1989 | Schreiber |
| 4,942,875 A | 7/1990 | Hlavacek et al. |
| 4,946,467 A | 8/1990 | Ohi et al. |
| 4,960,420 A | 10/1990 | Goble et al. |
| 4,983,184 A | 1/1991 | Steinemann |
| 5,047,103 A | 9/1991 | Abrams et al. |
| 5,061,283 A | 10/1991 | Silvestrini |
| 5,163,956 A | 11/1992 | Liu et al. |
| 5,207,841 A | 5/1993 | Abrams |
| 5,209,756 A | 5/1993 | Seedhom et al. |
| 5,250,049 A | 10/1993 | Michael |
| 5,290,552 A | 3/1994 | Sierra et al. |
| 5,292,334 A | 3/1994 | Howansky |
| 5,306,290 A | 4/1994 | Martins et al. |
| 5,306,500 A | 4/1994 | Rhee et al. |
| 5,312,023 A | 5/1994 | Green et al. |
| 5,326,013 A | 7/1994 | Green et al. |
| 5,329,943 A | 7/1994 | Johnson |
| 5,342,376 A | 8/1994 | Ruff |
| 5,346,746 A | 9/1994 | Abrams |
| 5,370,662 A | 12/1994 | Stone et al. |
| 5,389,098 A | 2/1995 | Tsuruta et al. |
| 5,413,791 A | 5/1995 | Rhee et al. |
| 5,446,091 A | 8/1995 | Rhee et al. |
| 5,447,265 A | 9/1995 | Vidal et al. |
| 5,458,636 A | 10/1995 | Brancato |
| 5,465,894 A | 11/1995 | Clark et al. |
| 5,480,644 A | 1/1996 | Freed |
| 5,510,418 A | 4/1996 | Rhee et al. |
| 5,523,348 A | 6/1996 | Rhee et al. |
| 5,527,341 A | 6/1996 | Gogolewski et al. |
| 5,542,594 A | 8/1996 | McKean et al. |
| 5,556,428 A | 9/1996 | Shah |
| 5,575,803 A | 11/1996 | Cooper et al. |
| 5,580,923 A | 12/1996 | Yeung et al. |
| 55,973,637 | 1/1997 | Abrams et al. |
| 5,603,443 A | 2/1997 | Clark et al. |
| 5,607,094 A | 3/1997 | Clark et al. |
| 5,630,824 A | 5/1997 | Hart |
| 5,630,842 A | 5/1997 | Brodniewicz |
| 5,649,937 A | 7/1997 | Bito et al. |
| 5,665,112 A | 9/1997 | Thal |
| 5,667,839 A | 9/1997 | Berg |
| 5,706,997 A | 1/1998 | Green et al. |
| 5,711,472 A | 1/1998 | Bryan |
| 5,713,903 A | 2/1998 | Sander et al. |
| 5,716,981 A | 2/1998 | Hunter et al. |
| 5,723,008 A | 3/1998 | Gordon |
| 5,728,110 A | 3/1998 | Vidal et al. |
| 5,732,871 A | 3/1998 | Clark et al. |
| 5,756,678 A | 5/1998 | Shenoy et al. |
| 5,766,250 A | 6/1998 | Chervitz et al. |
| 5,785,713 A | 7/1998 | Jobe |
| 5,800,544 A | 9/1998 | Demopulos et al. |
| 5,807,581 A | 9/1998 | Rosenblatt et al. |
| 5,840,078 A * | 11/1998 | Yerys .................. A61F 2/0811 411/184 |
| 5,858,156 A | 1/1999 | Abrams et al. |
| 5,860,229 A | 1/1999 | Morgenstern |
| 5,865,361 A | 2/1999 | Milliman et al. |
| 5,908,427 A | 6/1999 | McKean et al. |
| 5,916,224 A | 6/1999 | Esplin |
| 5,947,999 A | 9/1999 | Groiso |
| 5,961,520 A | 10/1999 | Beck, Jr. et al. |
| 5,964,774 A | 10/1999 | McKean et al. |
| 5,980,524 A | 11/1999 | Justin et al. |
| 5,997,811 A | 12/1999 | Esposito |
| 6,010,764 A | 1/2000 | Abrams |
| 6,013,083 A | 1/2000 | Bennett |
| 6,027,523 A | 2/2000 | Schmieding |
| 6,030,410 A | 2/2000 | Zurbrugg |
| 6,045,560 A | 4/2000 | McKean et al. |
| 6,079,606 A | 6/2000 | Milliman et al. |
| 6,080,192 A | 6/2000 | Demopulos et al. |
| 6,083,242 A | 7/2000 | Cook |
| 6,083,332 A | 7/2000 | Abrams |
| 6,086,547 A | 7/2000 | Hanssen et al. |
| 6,099,538 A | 8/2000 | Moses et al. |
| 6,106,556 A | 8/2000 | Demopulos et al. |
| 6,110,560 A | 8/2000 | Abrams |
| 6,111,165 A | 8/2000 | Berg |
| 6,206,886 B1 | 3/2001 | Bennett |
| 6,241,139 B1 | 6/2001 | Milliman et al. |
| 6,241,747 B1 | 6/2001 | Ruff |
| 6,250,532 B1 | 6/2001 | Green et al. |
| 6,277,394 B1 | 8/2001 | Sierra |
| 6,330,965 B1 | 12/2001 | Milliman et al. |
| 6,333,347 B1 | 12/2001 | Hunter et al. |
| 6,358,557 B1 | 3/2002 | Wang et al. |
| 6,383,199 B2 | 5/2002 | Carter et al. |
| 6,413,742 B1 | 7/2002 | Olsen et al. |
| D462,766 S | 9/2002 | Jacobs et al. |
| 6,464,706 B1 * | 10/2002 | Winters ................ A61B 17/68 623/13.14 |
| 6,472,171 B1 | 10/2002 | Toman et al. |
| 6,485,503 B2 | 11/2002 | Jacobs et al. |
| 6,491,714 B1 | 12/2002 | Bennett |
| 6,495,127 B1 | 12/2002 | Wallace et al. |
| 6,515,016 B2 | 2/2003 | Hunter |
| 6,517,579 B1 | 2/2003 | Paulos et al. |
| 6,533,802 B2 | 3/2003 | Bojarski et al. |
| 6,544,273 B1 | 4/2003 | Harari et al. |
| 6,551,315 B2 | 4/2003 | Kortenbach et al. |
| 6,569,186 B1 | 5/2003 | Winters et al. |
| 6,575,976 B2 | 6/2003 | Grafton |
| 6,644,532 B2 | 11/2003 | Green et al. |
| 6,645,226 B1 | 11/2003 | Jacobs et al. |
| 6,648,893 B2 | 11/2003 | Dudasik |
| 6,652,563 B2 | 11/2003 | Dreyfuss |

(56) References Cited

U.S. PATENT DOCUMENTS

| | | |
|---|---|---|
| 6,656,183 B2 | 12/2003 | Colleran et al. |
| 6,666,873 B1 | 12/2003 | Cassell |
| 6,669,073 B2 | 12/2003 | Milliman et al. |
| 6,689,803 B2 | 2/2004 | Hunter |
| 6,712,830 B2 | 3/2004 | Esplin |
| 6,716,226 B2 | 4/2004 | Sixto, Jr. et al. |
| 6,740,100 B2 | 5/2004 | Demopulos et al. |
| 6,743,233 B1 | 6/2004 | Baldwin et al. |
| 6,743,240 B2 | 6/2004 | Smith et al. |
| 6,773,450 B2 | 8/2004 | Leung et al. |
| 6,824,548 B2 | 11/2004 | Smith et al. |
| 6,830,174 B2 | 12/2004 | Hillstead et al. |
| 6,843,794 B2 | 1/2005 | Sixto, Jr. et al. |
| 6,877,647 B2 | 4/2005 | Green et al. |
| 6,893,452 B2 | 5/2005 | Jacobs |
| 6,905,513 B1 | 6/2005 | Metzger |
| 6,945,979 B2 | 9/2005 | Kortenbach et al. |
| 6,953,138 B1 | 10/2005 | Dworak et al. |
| 6,953,139 B2 | 10/2005 | Milliman et al. |
| 6,962,594 B1 | 11/2005 | Thevenet |
| 6,991,643 B2 | 1/2006 | Saadat |
| 7,016,194 B1 | 3/2006 | Wong |
| 7,056,331 B2 | 6/2006 | Kaplan et al. |
| 7,070,602 B2 | 7/2006 | Smith et al. |
| 7,074,203 B1 | 7/2006 | Johanson et al. |
| 7,090,685 B2 | 8/2006 | Kortenbach et al. |
| 7,121,446 B2 | 10/2006 | Arad et al. |
| 7,129,209 B2 | 10/2006 | Rhee |
| 7,156,862 B2 | 1/2007 | Jacobs et al. |
| 7,172,615 B2 | 2/2007 | Morriss et al. |
| 7,176,256 B2 | 2/2007 | Rhee et al. |
| 7,189,238 B2 | 3/2007 | Lombardo et al. |
| 7,226,468 B2 | 6/2007 | Ruff |
| 7,229,413 B2 | 6/2007 | Violante et al. |
| 7,232,445 B2 | 6/2007 | Kortenbach et al. |
| 7,275,674 B2 | 10/2007 | Racenet et al. |
| 7,296,724 B2 | 11/2007 | Green et al. |
| 7,303,107 B2 | 12/2007 | Milliman et al. |
| 7,303,577 B1 | 12/2007 | Dean |
| 7,309,346 B2 | 12/2007 | Martinek |
| 7,328,829 B2 | 2/2008 | Arad et al. |
| 7,343,920 B2 | 3/2008 | Toby et al. |
| 7,354,627 B2 | 4/2008 | Pedrozo et al. |
| 7,398,907 B2 | 7/2008 | Racenet et al. |
| 7,401,720 B1 | 7/2008 | Durrani |
| 7,438,209 B1 | 10/2008 | Hess et al. |
| 7,442,202 B2 | 10/2008 | Dreyfuss |
| 7,464,848 B2 | 12/2008 | Green et al. |
| 7,510,566 B2 | 3/2009 | Jacobs et al. |
| 7,530,484 B1 | 5/2009 | Durrani |
| 7,530,990 B2 | 5/2009 | Perriello et al. |
| 7,565,993 B2 | 7/2009 | Milliman et al. |
| 7,568,604 B2 | 8/2009 | Ehrenfels et al. |
| 7,600,663 B2 | 10/2009 | Green |
| 7,604,151 B2 | 10/2009 | Hess et al. |
| 7,611,038 B2 | 11/2009 | Racenet et al. |
| 7,611,521 B2 | 11/2009 | Lubbers et al. |
| 7,615,058 B2 | 11/2009 | Sixto, Jr. et al. |
| 7,624,487 B2 | 12/2009 | Trull et al. |
| 7,635,074 B2 | 12/2009 | Olson et al. |
| 7,635,367 B2 | 12/2009 | Groiso |
| 7,640,617 B2 | 1/2010 | Kennedy et al. |
| 7,641,091 B2 | 1/2010 | Olson et al. |
| 7,665,646 B2 | 2/2010 | Prommersberger |
| 7,708,759 B2 | 5/2010 | Lubbers et al. |
| 7,727,246 B2 | 6/2010 | Sixto, Jr. et al. |
| 7,727,248 B2 | 6/2010 | Smith et al. |
| 7,731,718 B2 | 6/2010 | Schwammberger et al. |
| 7,771,468 B2 | 8/2010 | Whitbourne et al. |
| 7,794,484 B2 | 9/2010 | Stone et al. |
| 7,819,896 B2 | 10/2010 | Racenet |
| 7,824,426 B2 | 11/2010 | Racenet et al. |
| 7,828,189 B2 | 11/2010 | Holsten et al. |
| 7,842,097 B2 | 11/2010 | Yamamoto et al. |
| 7,845,533 B2 | 12/2010 | Marczyk et al. |
| 7,861,907 B2 | 1/2011 | Green et al. |
| 7,887,551 B2 | 2/2011 | Bojarski et al. |
| 7,891,531 B1 | 2/2011 | Ward |
| 7,909,224 B2 | 3/2011 | Prommersberger |
| 7,926,692 B2 | 4/2011 | Racenet et al. |
| 7,942,304 B2 | 5/2011 | Taylor et al. |
| 7,942,885 B2 | 5/2011 | Sixto, Jr. et al. |
| 7,950,561 B2 | 5/2011 | Aranyi |
| 3,006,700 A1 | 8/2011 | Demopulos et al. |
| 3,008,598 A1 | 8/2011 | Whitman et al. |
| 3,016,177 A1 | 9/2011 | Bettuchi et al. |
| 3,016,178 A1 | 9/2011 | Olson et al. |
| 3,021,378 A1 | 9/2011 | Sixto, Jr. et al. |
| 8,011,550 B2 | 9/2011 | Aranyi et al. |
| 8,029,563 B2 | 10/2011 | House et al. |
| 8,033,439 B2 | 10/2011 | Racenet et al. |
| 8,038,045 B2 | 10/2011 | Bettuchi et al. |
| 8,043,328 B2 | 10/2011 | Hahnen et al. |
| 3,057,524 A1 | 11/2011 | Meridew |
| 8,062,314 B2 | 11/2011 | Sixto, Jr. et al. |
| 8,062,330 B2 | 11/2011 | Prommersberger et al. |
| 8,062,363 B2 | 11/2011 | Hirpara et al. |
| 8,066,721 B2 | 11/2011 | Kortenbach et al. |
| 8,070,033 B2 | 12/2011 | Milliman et al. |
| 8,083,118 B2 | 12/2011 | Milliman et al. |
| 8,083,119 B2 | 12/2011 | Prommersberger |
| 8,083,120 B2 | 12/2011 | Shelton, Iv et al. |
| 8,087,563 B2 | 1/2012 | Milliman |
| 8,113,409 B2 | 2/2012 | Cohen et al. |
| 8,114,129 B2 | 2/2012 | Lubbers et al. |
| 8,118,834 B1 | 2/2012 | Goraltchouk et al. |
| 8,123,101 B2 | 2/2012 | Racen et al. |
| 8,141,762 B2 | 3/2012 | Bedi et al. |
| 8,157,151 B2 | 4/2012 | Ingmanson et al. |
| 8,186,557 B2 | 5/2012 | Cohen et al. |
| 8,186,560 B2 | 5/2012 | Hess et al. |
| 8,205,620 B2 | 6/2012 | Taylor et al. |
| 8,210,414 B2 | 7/2012 | Bettuchi et al. |
| 8,210,416 B2 | 7/2012 | Milliman et al. |
| 8,256,654 B2 | 9/2012 | Bettuchi et al. |
| 8,256,656 B2 | 9/2012 | Milliman et al. |
| 8,292,152 B2 | 10/2012 | Milliman et al. |
| 8,298,286 B2 | 10/2012 | Trieu |
| 8,308,041 B2 | 11/2012 | Kostrzewski |
| 8,308,042 B2 | 11/2012 | Aranyi |
| 8,308,046 B2 | 11/2012 | Prommersberger |
| 8,322,455 B2 | 12/2012 | Shelton, IV et al. |
| 8,328,061 B2 | 12/2012 | Kasvikis |
| 8,342,377 B2 | 1/2013 | Milliman et al. |
| 8,343,186 B2 | 1/2013 | Dreyfuss et al. |
| 8,348,129 B2 | 1/2013 | Bedi et al. |
| 8,439,936 B2 | 5/2013 | McClellan |
| 8,453,905 B2 | 6/2013 | Holcomb et al. |
| 8,453,910 B2 | 6/2013 | Bettuchi et al. |
| 8,464,925 B2 | 6/2013 | Hull et al. |
| 8,469,252 B2 | 6/2013 | Holcomb et al. |
| 8,480,692 B2 | 7/2013 | McClellan |
| 8,485,412 B2 | 7/2013 | Shelton, IV et al. |
| 8,491,600 B2 | 7/2013 | McDevitt et al. |
| 8,500,776 B2 | 8/2013 | Ebner |
| 8,518,091 B2 | 8/2013 | McDevitt et al. |
| 8,540,131 B2 | 9/2013 | Swayze |
| 8,550,325 B2 | 10/2013 | Cohen et al. |
| 8,574,275 B2 | 11/2013 | Stone et al. |
| 8,585,721 B2 | 11/2013 | Kirsch |
| 8,602,286 B2 | 12/2013 | Crainich et al. |
| 8,608,765 B1 | 12/2013 | Jurbala |
| 8,613,384 B2 | 12/2013 | Pastorelli et al. |
| 8,616,430 B2 | 12/2013 | (Prommersberger) Stopek |
| 8,623,052 B2 | 1/2014 | Dreyfuss et al. |
| 8,636,766 B2 | 1/2014 | Milliman et al. |
| 8,668,130 B2 | 3/2014 | Hess et al. |
| 8,684,249 B2 | 4/2014 | Racenet et al. |
| 8,720,766 B2 | 5/2014 | Hess et al. |
| 8,740,034 B2 | 6/2014 | Morgan et al. |
| 8,801,732 B2 | 8/2014 | Harris et al. |
| 8,801,755 B2 | 8/2014 | Dreyfuss et al. |
| 8,814,904 B2 | 8/2014 | Bennett |
| 8,834,543 B2 | 9/2014 | McDevitt et al. |

(56) References Cited

U.S. PATENT DOCUMENTS

| | | |
|---|---|---|
| 8,840,003 B2 | 9/2014 | Morgan et al. |
| 8,845,686 B2 | 9/2014 | Bennett |
| 8,905,287 B2 | 12/2014 | Racenet et al. |
| 8,939,983 B2 | 1/2015 | Stone et al. |
| 9,204,960 B2 | 12/2015 | Albertorio et al. |
| 9,277,909 B2 | 3/2016 | Brunsvold |
| 9,307,979 B1 | 4/2016 | Bennett et al. |
| 9,427,309 B2 | 8/2016 | Kubiak et al. |
| 9,439,645 B2 | 9/2016 | Stone et al. |
| 9,451,961 B2 | 9/2016 | Kubiak |
| 9,486,207 B2 | 11/2016 | Dooney, Jr. et al. |
| 9,642,610 B2 | 5/2017 | Albertorio et al. |
| 9,655,625 B2 | 5/2017 | Kubiak et al. |
| 9,700,305 B2 | 7/2017 | Bennett et al. |
| 10,219,804 B2 | 3/2019 | Linder et al. |
| 10,299,842 B2 | 5/2019 | Hollis et al. |
| 10,835,241 B2 | 11/2020 | Kubiak et al. |
| 2001/0044637 A1 | 11/2001 | Jacobs et al. |
| 2001/0051815 A1 | 12/2001 | Esplin |
| 2002/0013298 A1 | 1/2002 | Hunter |
| 2002/0022861 A1 | 2/2002 | Jacobs et al. |
| 2002/0055666 A1 | 5/2002 | Hunter et al. |
| 2002/0077661 A1 | 6/2002 | Saadat |
| 2002/0123750 A1 | 9/2002 | Eisermann et al. |
| 2002/0173807 A1 | 11/2002 | Jacobs |
| 2002/0192280 A1 | 12/2002 | Hunter et al. |
| 2003/0065360 A1 | 4/2003 | Jacobs et al. |
| 2003/0069602 A1 | 4/2003 | Jacobs et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130735 A1 | 7/2003 | Rogalski |
| 2003/0153972 A1 | 8/2003 | Helmus |
| 2003/0157170 A1 | 8/2003 | Liggins et al. |
| 2003/0181371 A1 | 9/2003 | Hunter et al. |
| 2003/0203976 A1 | 10/2003 | Hunter et al. |
| 2004/0006352 A1 | 1/2004 | Nobles et al. |
| 2004/0010276 A1 | 1/2004 | Jacobs et al. |
| 2004/0039404 A1 | 2/2004 | Dreyfuss |
| 2004/0059336 A1 | 3/2004 | Lombardo et al. |
| 2004/0060410 A1 | 4/2004 | Leung et al. |
| 2004/0076672 A1 | 4/2004 | Hunter et al. |
| 2004/0088003 A1 | 5/2004 | Leung et al. |
| 2004/0153153 A1 | 8/2004 | Elson et al. |
| 2004/0193217 A1 | 9/2004 | Lubbers et al. |
| 2004/0199241 A1 | 10/2004 | Gravett et al. |
| 2004/0219214 A1 | 11/2004 | Gravett et al. |
| 2004/0220591 A1 | 11/2004 | Bonutti |
| 2004/0220616 A1 | 11/2004 | Bonutti et al. |
| 2004/0224023 A1 | 11/2004 | Hunter et al. |
| 2004/0254609 A1 | 12/2004 | Esplin |
| 2004/0260340 A1 | 12/2004 | Jacobs et al. |
| 2004/0267362 A1 | 12/2004 | Hwang et al. |
| 2005/0090827 A1 | 4/2005 | Gedebou |
| 2005/0152941 A1 | 7/2005 | Hunter et al. |
| 2005/0175665 A1 | 8/2005 | Hunter et al. |
| 2005/0186261 A1 | 8/2005 | Avelar et al. |
| 2005/0192428 A1 | 9/2005 | Berg et al. |
| 2005/0197699 A1 | 9/2005 | Jacobs et al. |
| 2006/0127445 A1 | 6/2006 | Hunter et al. |
| 2006/0135994 A1 | 6/2006 | Ruff et al. |
| 2006/0147332 A1 | 7/2006 | Jones |
| 2006/0149349 A1 | 7/2006 | Garbe |
| 2006/0240064 A9 | 10/2006 | Hunter et al. |
| 2006/0240113 A1 | 10/2006 | Hunter et al. |
| 2006/0247641 A1 | 11/2006 | Re et al. |
| 2007/0021779 A1 | 1/2007 | Garvin et al. |
| 2007/0026043 A1 | 2/2007 | Guan et al. |
| 2007/0027527 A1 | 2/2007 | Williams et al. |
| 2007/0065663 A1 | 3/2007 | Trull et al. |
| 2007/0123984 A1 | 5/2007 | Hodorek |
| 2007/0156158 A1 | 7/2007 | Herzberg et al. |
| 2007/0162022 A1 | 7/2007 | Zhang et al. |
| 2007/0196421 A1 | 8/2007 | Hunter et al. |
| 2007/0208355 A1 | 9/2007 | Ruff |
| 2007/0208377 A1 | 9/2007 | Kaplan et al. |
| 2008/0003394 A1 | 1/2008 | Eke |
| 2008/0027443 A1 | 1/2008 | Lambert |
| 2008/0027445 A1 | 1/2008 | Brown, Jr. et al. |
| 2008/0027446 A1 | 1/2008 | Stone et al. |
| 2008/0027486 A1 | 1/2008 | Jones et al. |
| 2008/0051888 A1 | 2/2008 | Ratcliffe et al. |
| 2008/0058579 A1 | 3/2008 | Hunter et al. |
| 2008/0124400 A1 | 5/2008 | Liggins et al. |
| 2008/0195204 A1 | 8/2008 | Zhukauskas et al. |
| 2008/0234731 A1 | 9/2008 | Leung et al. |
| 2008/0247987 A1 | 10/2008 | Liggins et al. |
| 2008/0281325 A1 | 11/2008 | Stone et al. |
| 2008/0312315 A1 | 12/2008 | Daniloff et al. |
| 2009/0012560 A1 | 1/2009 | Hunter et al. |
| 2009/0018577 A1 | 1/2009 | Leung et al. |
| 2009/0020584 A1 | 1/2009 | Soltz et al. |
| 2009/0048537 A1 | 2/2009 | Lydon et al. |
| 2009/0048616 A1 | 2/2009 | Gonzalez-Hernandez |
| 2009/0060973 A1 | 3/2009 | Hunter et al. |
| 2009/0107965 A1 | 4/2009 | D'Agostino |
| 2009/0112259 A1 | 4/2009 | D'Agostino |
| 2009/0117070 A1 | 5/2009 | Daniloff et al. |
| 2009/0125094 A1 | 5/2009 | Rust |
| 2009/0143819 A1 | 6/2009 | D'Agostino |
| 2009/0149884 A1 | 6/2009 | Snyder et al. |
| 2009/0156980 A1 | 6/2009 | Eaton et al. |
| 2009/0216326 A1 | 8/2009 | Hirpara et al. |
| 2009/0222039 A1 | 9/2009 | Dreyfuss et al. |
| 2009/0226500 A1 | 9/2009 | Avelar et al. |
| 2009/0228021 A1 | 9/2009 | Leung |
| 2009/0234386 A1 | 9/2009 | Dean et al. |
| 2009/0280153 A1 | 11/2009 | Hunter et al. |
| 2009/0299386 A1* | 12/2009 | Meridew ............ A61F 2/0811 606/232 |
| 2009/0324720 A1 | 12/2009 | He et al. |
| 2010/0016872 A1 | 1/2010 | Bayton et al. |
| 2010/0023052 A1 | 1/2010 | Heinrich et al. |
| 2010/0160718 A1 | 6/2010 | Villafana et al. |
| 2010/0193568 A1 | 8/2010 | Scheib et al. |
| 2010/0217314 A1 | 8/2010 | Holsten et al. |
| 2010/0228078 A1 | 9/2010 | Sater |
| 2010/0249802 A1 | 9/2010 | May et al. |
| 2010/0324676 A1 | 12/2010 | Albertorio et al. |
| 2011/0106253 A1 | 5/2011 | Barwood et al. |
| 2011/0124956 A1 | 5/2011 | Mujwid |
| 2011/0125287 A1 | 5/2011 | Hotter et al. |
| 2011/0155787 A1 | 6/2011 | Baxter, III et al. |
| 2011/0288565 A1 | 11/2011 | Kubiak et al. |
| 2011/0288566 A1 | 11/2011 | Kubiak |
| 2011/0301706 A1 | 12/2011 | Brooks et al. |
| 2012/0080336 A1 | 4/2012 | Shelton, IV et al. |
| 2012/0130374 A1 | 5/2012 | Bouduban et al. |
| 2012/0203253 A1 | 8/2012 | Kubiak |
| 2012/0245629 A1 | 9/2012 | Gross et al. |
| 2013/0131781 A1 | 5/2013 | Greenhalgh et al. |
| 2013/0144310 A1 | 6/2013 | Gordon et al. |
| 2013/0197580 A1 | 8/2013 | Perriello et al. |
| 2014/0039551 A1 | 2/2014 | Donahue |
| 2014/0067061 A1 | 3/2014 | Kubiak et al. |
| 2014/0214037 A1 | 7/2014 | Mayer et al. |
| 2015/0245841 A1 | 9/2015 | Linder et al. |
| 2015/0272567 A1 | 10/2015 | Feezor et al. |
| 2015/0289866 A1 | 10/2015 | Bowen et al. |
| 2016/0066900 A1 | 3/2016 | Brunsvold et al. |
| 2016/0066907 A1 | 3/2016 | Cheney et al. |
| 2016/0100835 A1 | 4/2016 | Linder et al. |
| 2016/0100933 A1 | 4/2016 | Linder et al. |
| 2016/0174965 A1 | 6/2016 | Brunsvold |
| 2016/0242771 A1* | 8/2016 | Weinstein ............ A61B 17/842 |
| 2017/0027578 A1 | 2/2017 | Friedman et al. |
| 2017/0056158 A1 | 3/2017 | Saing |
| 2017/0156847 A1 | 6/2017 | Ricci et al. |
| 2017/0333026 A1 | 11/2017 | Dreyfuss et al. |

(56) References Cited

U.S. PATENT DOCUMENTS

2018/0078253 A1 3/2018 Kubiak et al.
2018/0200042 A1 7/2018 Kubiak et al.
2021/0100545 A1* 4/2021 Thies ................ A61B 17/0401

OTHER PUBLICATIONS

Supplementary European Search Report issued in EP 15850646.9 dated Jun. 25, 2018.
International Search Report dated Feb. 26, 2016 for International Application No. PCT/US2015/56059 (14 pages).
International Search Report dated Jul. 20, 2015 for International Application No. PCT/US2015/020231 (10 pages).
International Search Report dated Oct. 10, 2013 for International Application No. PCT/US2013/052735 (7 pages).
Mckenzie, "An Experimental Multiple Barbed Suture For The Long Flexor Tendons Of The Palm And Fingers," Journal of Bone and Joint Surgery, Aug. 1967, pp. 440-447, vol. 49 B, No. 3.
Momose et al., "Suture Techniques With High Breaking Strength And Low Gliding Resistance: Experiments In The Dog Flexor Digitorum Pofundus Tendon," Acta Orthop Scand, 2001, 72(6):635-641.
Leung et al., "Barbed, Bi-Directional Medical Sutures: Biomechanical Properties And Wound Closure Efficacy Study," Society for Biomaterials 28ths Annual Meeting Transactions, 2002, p. 724.
Chunfeng et al., "Enhancing The Strength Of The Tendon-Suture Interface Using 1-Ethyl-3-(3-dimethylaminoproply) Carbodimide Hydrochloride And Cyanoacrylate," Journal of Hand Surger, 2007, 32(5): 606-11.
Burkhead et al., "Use Of Graft Jacket As An Augmentation For Massive Rotator Cuff Tears," Semin Arthro, 2007, 18 (1): 11-18.
Hirpara et al., "A Barbed Device For Digital Flexor Tendon Repair," http://proceedings.jbjs.org.uk/cgi/content/abstract/92-B/SUPP_II/291-d, Mar. 2010.
Office Action issued in EP 15850646.9 dated Sep. 19, 2019.
International Search Report dated May 8, 2019 for International Application No. PCT/US2019/018628 (14 pages).
Supplementary European Search Report dated Oct. 20, 2021 for European App. No. 19756761 (10 pages).

* cited by examiner

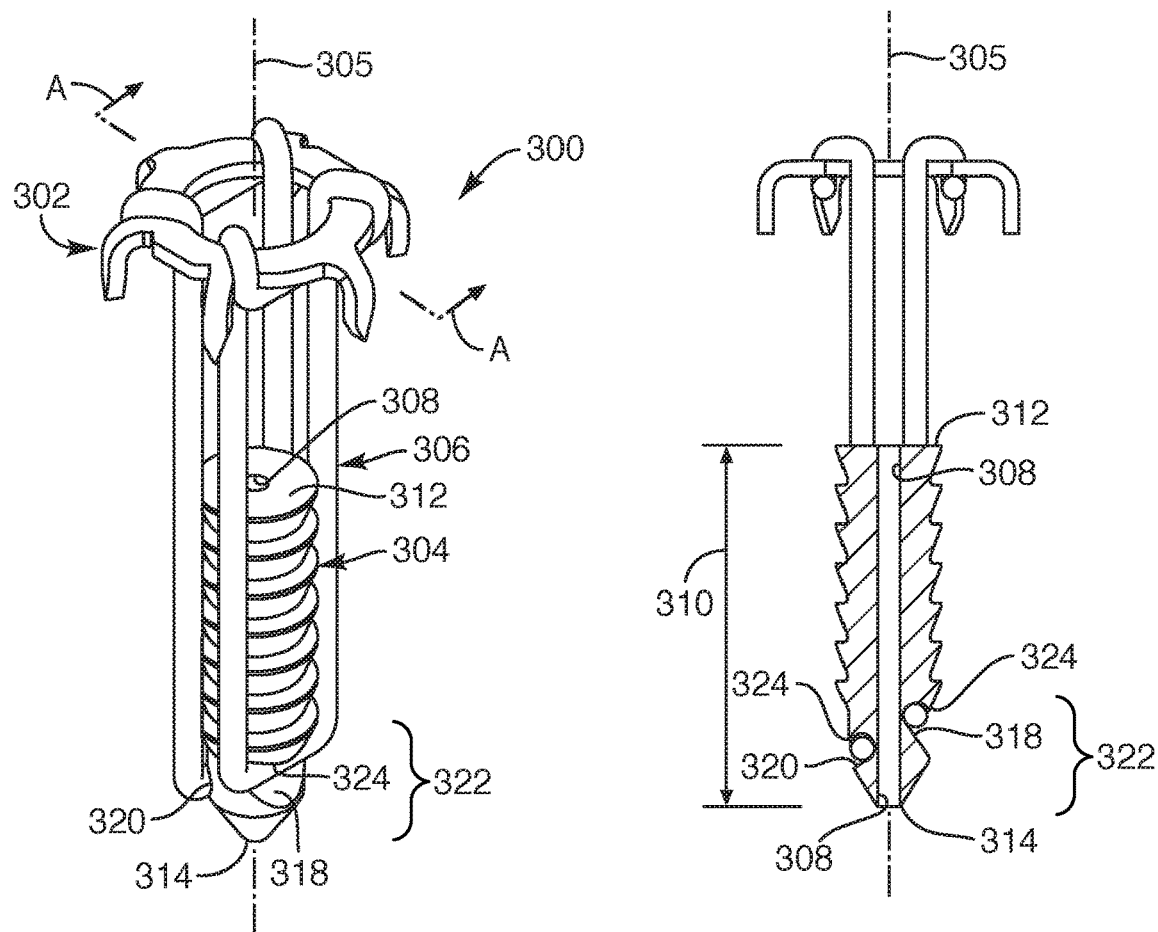
FIG. 14
FIG. 14A
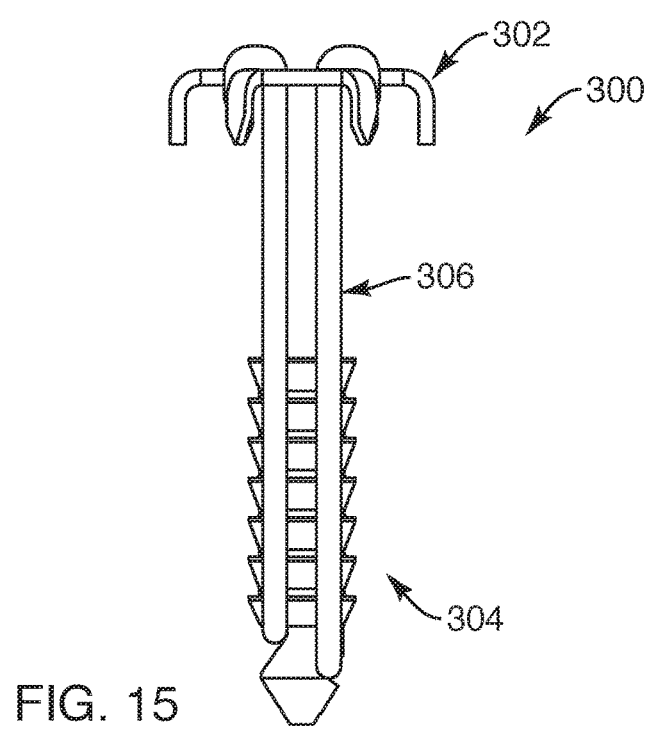
FIG. 15

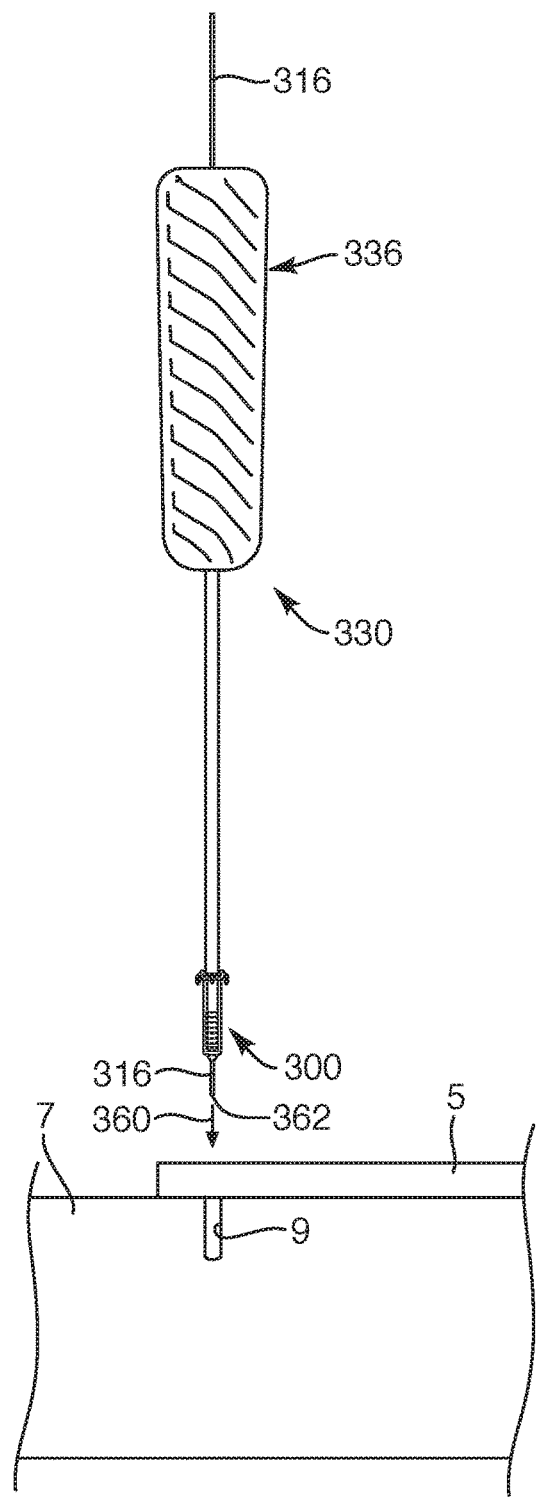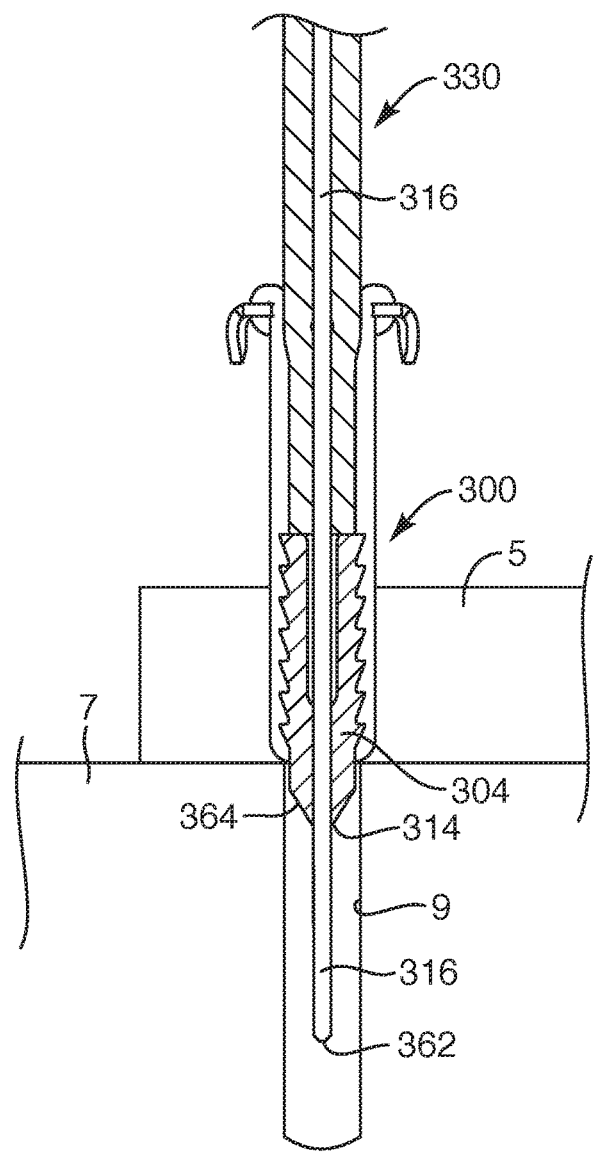
FIG. 17
FIG. 18

DEVICES, SYSTEMS, AND METHODS FOR REPAIRING SOFT TISSUE AND ATTACHING SOFT TISSUE TO BONE

CROSS-REFERENCE TO RELATED APPLICATIONS

The present application claims the benefit, and is a continuation-in-part of, U.S. patent application Ser. No. 16/279,337, filed Feb. 19, 2019, the disclosure of which is hereby incorporated by reference in its entirety. Further, U.S. patent application Ser. No. 16/279,337 claims the benefit of U.S. Provisional Application No. 62/633,000, filed Feb. 20, 2018, the disclosure of which is hereby incorporated by reference in its entirety. Further, U.S. patent application Ser. No. 16/279,337 also claims the benefit, and is a continuation-in-part of, U.S. patent application Ser. No. 16/226,573, filed Dec. 19, 2018, which claims benefit of U.S. Provisional Application No. 62/608,533, filed Dec. 20, 2017, and U.S. Provisional Application No. 62/633,000, filed Feb. 20, 2018, the disclosures of each are hearby incorporated by reference in their entirety.

TECHNICAL FIELD

The present invention relates generally to soft tissue repair sites. More particularly, the present invention relates to devices, systems, and methods for repairing soft tissue and attaching soft tissue to bone.

BACKGROUND

One of the most common needs in orthopedic surgery is the fixation of soft tissue, such as ligament or tendon, to bone. Typically, fixating soft tissue to bone is implemented with a bone anchor and suture material with suture coupled between the soft tissue and the bone anchor such that the soft tissue is cinched in against the bone. However, coupling suture to soft tissue is time consuming and often requires complex suture patterns for effective fixation, often requiring specialized surgeons. While this can provide a good initial repair, the strength and quality of the repair may quickly degrade with subsequent loading and mobilization, often resulting is subsequent procedures depending on the activity level of the patient. As such, it would be advantageous to eliminate the complexity and the time consuming nature of this type of surgery while also increasing the long term effectiveness of the procedure.

BRIEF SUMMARY OF THE INVENTION

Embodiments of the present invention are directed to various devices, systems and methods for repairing soft tissue and attaching soft tissue to bone at a soft tissue repair site. For example, in one embodiment, a repair device system for fixating soft tissue to bone is provided. The repair device system includes a bone anchor, a soft tissue anchor, and one or more flexible members. The bone anchor includes an elongated structure extending between a proximal end and a distal end, the bone anchor defining a bone anchor axis extending along the elongated structure. Further, the bone anchor defines a hole therein extending between the proximal end and the distal end and along the bone anchor axis. The soft tissue anchor includes a base with multiple legs extending from the base so as to extend toward the bone anchor. The one or more flexible members extend to couple the soft tissue anchor to the bone anchor such that the one or more flexible members are sized and configured to substantially maintain the soft tissue anchor to be spaced relative to the bone anchor at a pre-determined distance.

In another embodiment, the bone anchor defines a first side notch and a second side notch positioned adjacent a distal end portion of the bone anchor, the first and second side notches being positioned along opposite sides of the bone anchor and sized and configured to hold the one or more flexible members to the bone anchor. In a further embodiment, the first side notch and the second side notch are positioned along the opposite sides of the bone anchor in an off-set manner relative to and along the bone anchor axis.

In another embodiment, as the bone anchor is seated into bone, the one or more flexible members facilitate the soft tissue anchor to simultaneously fixate the soft tissue against the bone. In still another embodiment, the base defines a central opening extending centrally through the base, the soft tissue anchor defining a tissue anchor axis extending axially relative to the central opening of the base, the tissue anchor axis configured to extend substantially co-axial with the bone anchor axis. In another embodiment, the one or more flexible members include two loop portions extending upward from the bone anchor to wrap around portions of the soft tissue anchor. In yet another embodiment, the base of the anchor extends with an upper surface and an underside surface to define an outer periphery therebetween, the legs extending directly from the outer periphery and extending with a bend so that the legs are configured to extend toward the bone anchor.

In accordance with another embodiment of the present invention, a medical device system for fixating soft tissue to bone is provided. The medical device system includes a delivery instrument and a repair device system. The delivery instrument includes an elongated portion that defines a delivery instrument axis such that the elongated portion extends between a distal impacting surface and a proximal impacting surface. The delivery instrument includes an alignment hole defined in the distal impacting surface that extends longitudinally along the delivery instrument axis. The repair device system is configured to be removably coupled to the delivery instrument. The repair device system includes a bone anchor, a soft tissue anchor and one or more flexible members. The bone anchor includes an elongated structure extending between a proximal end and a distal end. The bone anchor defines a bone anchor axis extending along the elongated structure, the bone anchor defining a hole therein extending between the proximal end and the distal end and along the bone anchor axis. The hole of the bone anchor is configured to correspond with and be aligned with the alignment hole of the delivery instrument. The soft tissue anchor includes a base with multiple legs extending from the base, the base defining a central opening defining a tissue anchor axis. The one or more flexible members extend to couple the soft tissue anchor to the bone anchor. With the repair device system being removably coupled to the delivery instrument, the elongated portion extends through the central opening of the soft tissue anchor and the distal impacting surface abuts against the proximal end of the bone anchor. With this arrangement, as the bone anchor is being implanted into bone, the one or more flexible members extend taut between the bone anchor and the soft tissue anchor to simultaneously pull the soft tissue anchor into the soft tissue.

In another embodiment, the medical device system may further include a guidewire configured to assist in delivering the repair device system with the delivery instrument, the guidewire sized and configured to be bi-linearly moveable within and through the alignment hole of the delivery instrument and the hole of the bone anchor. In another embodiment, the bone anchor defines a first side notch and a second side notch positioned adjacent a distal end portion of the bone anchor, the first and second side notches being positioned along opposite sides of the bone anchor and sized and configured to hold the one or more flexible members to the bone anchor. In a further embodiment, the first side notch and the second side notch are positioned along the opposite sides of the bone anchor in an off-set manner relative to and along the bone anchor axis.

In another embodiment, the repair device system is configured to be delivered with the delivery instrument such that the delivery instrument axis is substantially coaxial, or substantially parallel, with the bone anchor axis and the tissue anchor axis. In another embodiment, the one or more flexible members are a fixed length such that, upon the one or more flexible members being in a taut position, the one or more flexible members maintain a substantially fixed distance between the bone anchor and the soft tissue anchor in a pre-delivered state and a delivered state. In still another embodiment, the medical device system further includes a retainer element having a line positioned along an underside of the soft tissue anchor to position the one or more flexible members in a taut position and removably couple the repair device system to the delivery instrument.

In accordance with another embodiment of the present invention, a method of fixating soft tissue to bone is provided. The method includes the steps of: providing a bone anchor coupled to a soft tissue anchor with one or more flexible members such that the bone anchor is engaged with a distal impacting surface of a delivery instrument with the soft tissue anchor positioned proximally along the delivery instrument with the one or more flexible members extending along the delivery instrument between the bone anchor and soft tissue anchor; positioning a distal end of a guidewire through the soft tissue and into a pre-formed hole defined in the bone such that the soft tissue is positioned over the bone and the pre-formed hole, the guidewire extending through a co-extensive longitudinal hole of the delivery instrument and the bone anchor; aligning the bone anchor relative to the preformed hole in the bone such that the bone anchor and the delivery instrument move over the guidewire until a distal end of the bone anchor is positioned in an upper portion of the pre-formed hole; and applying a force to the bone anchor with the delivery instrument to drive the bone anchor into the pre-formed hole such that, as the bone anchor is being driven into the pre-formed hole, the one or more flexible members pull legs extending from a base of the soft tissue anchor into the soft tissue such that an underside of the base is positioned against an outer surface of the soft tissue to substantially fixate the soft tissue against the bone.

In another embodiment, the applying step includes driving the bone anchor into the pre-formed hole to substantially simultaneously couple the soft tissue anchor to the soft tissue such that the one or more flexible members maintain a substantially fixed distance between the bone anchor and the soft tissue anchor. In another embodiment, the method further includes the step of withdrawing the guidewire from at least the bone anchor prior to the step of applying the force to the bone anchor. In still another embodiment, the applying step includes pulling the legs of the soft tissue anchor into the soft tissue with the one or more flexible members coupled to the bone anchor so that the soft tissue anchor clamps down upon the soft tissue as the bone anchor is seated within the pre-formed hole. In another embodiment, the providing step includes providing a retainer element for removably coupling the bone anchor to the delivery instrument, the retainer element having a line extending along an underside of the soft tissue anchor so that the one or more flexible members are in a taut position. In yet another embodiment, the applying step includes maintaining the one or more flexible members in a taut position in a pre-delivered state and a delivered state such that the bone anchor and the soft tissue anchor maintain a substantially fixed distance from each other.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 14 is a perspective view of another embodiment of a repair device system, according to the present invention;

FIG. 14A is a cross-sectional view of the repair device system taken along section line A-A of FIG. 14, according to another embodiment of the present invention;

FIG. 15 is a side view of the repair device system of FIG. 14, according to another embodiment of the present invention;

FIG. 17 is a side view of the medical device system, depicting the system prior to implanting the repair device system in a pre-formed hole in bone and fixating soft tissue to the bone, according to another embodiment of the present invention;

FIG. 18 is an enlarged cross-sectional view of the medical device system, depicting a guidewire being positioned in the pre-formed hole in the bone with a bone anchor positioned adjacent the pre-formed hole, according to another embodiment of the present invention;

DETAILED DESCRIPTION OF THE INVENTION

Various embodiments are disclosed herein of a soft tissue repair device and system. Such repair device and system may be sized and configured to approximate and fuse, for example, soft tissue to bone. The various embodiments may provide structure that maintains the soft tissue against bone in an abutting relationship, without gapping. In this manner, the repair device and system of the present invention may provide the proper healing required for fusing the soft tissue to bone.

Figure 1:
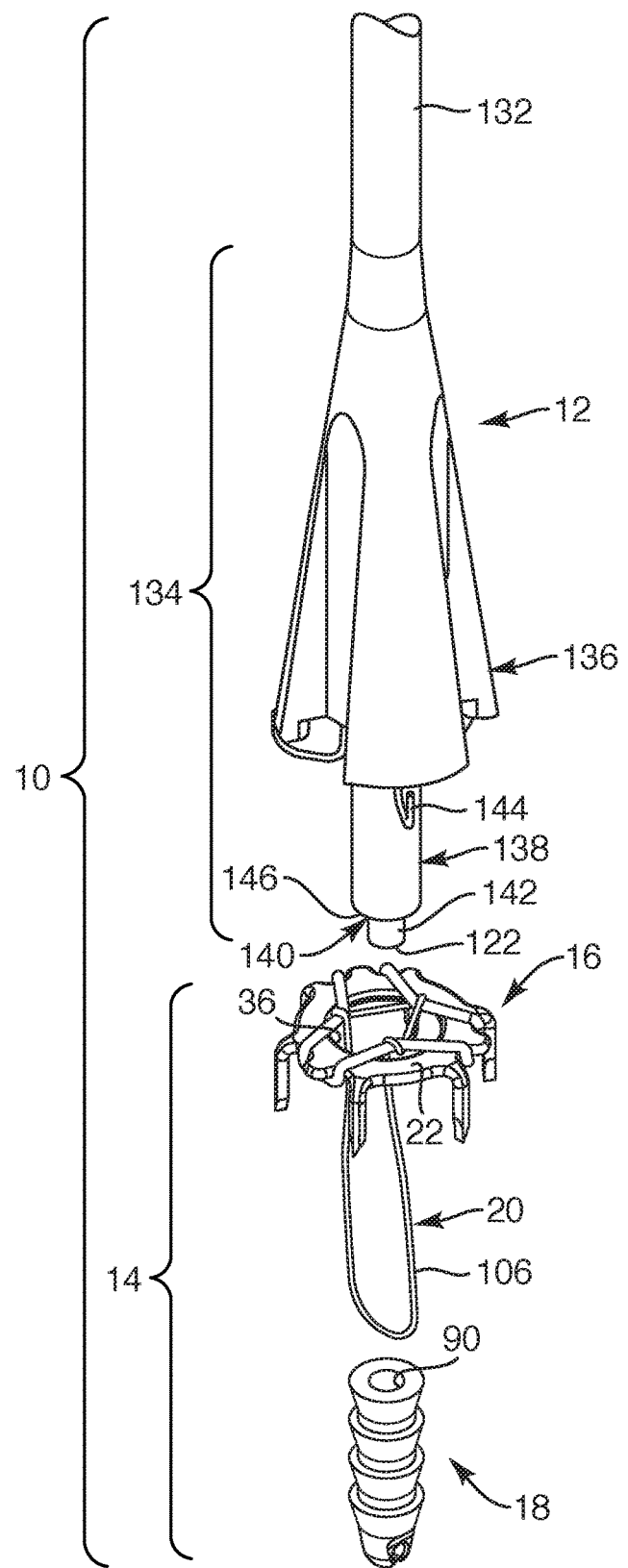
FIG. 1 is a perspective exploded view of a medical device system, depicting a repair device system and a delivery instrument, according to one embodiment of the present invention.

With reference to FIG. 1, one embodiment of a medical device system 10, shown in an exploded state, is provided. Such medical device system 10 may be employed to fixate soft tissue, such as tendon and ligament, to bone. The medical device system 10 may include a delivery instrument 12 and a repair device system 14, the delivery instrument 12 designed to facilitate anchoring a repair device or repair device system 14 to soft tissue and to bone. The repair device system 14 may include a soft tissue anchor 16 configured to be associated with or coupled to a bone anchor 18. In one embodiment, the soft tissue anchor 16 may be coupled to the bone anchor 18 with one or more flexible members 20. Upon assembling the medical device system 10, the repair device system 14 may be sized and configured to fixate soft tissue to bone such that, as the bone anchor 18 is being seated and anchored into bone, the soft tissue anchor 16 may be simultaneously seated and anchored to soft tissue (see FIGS. 5-6).

Figure 2:
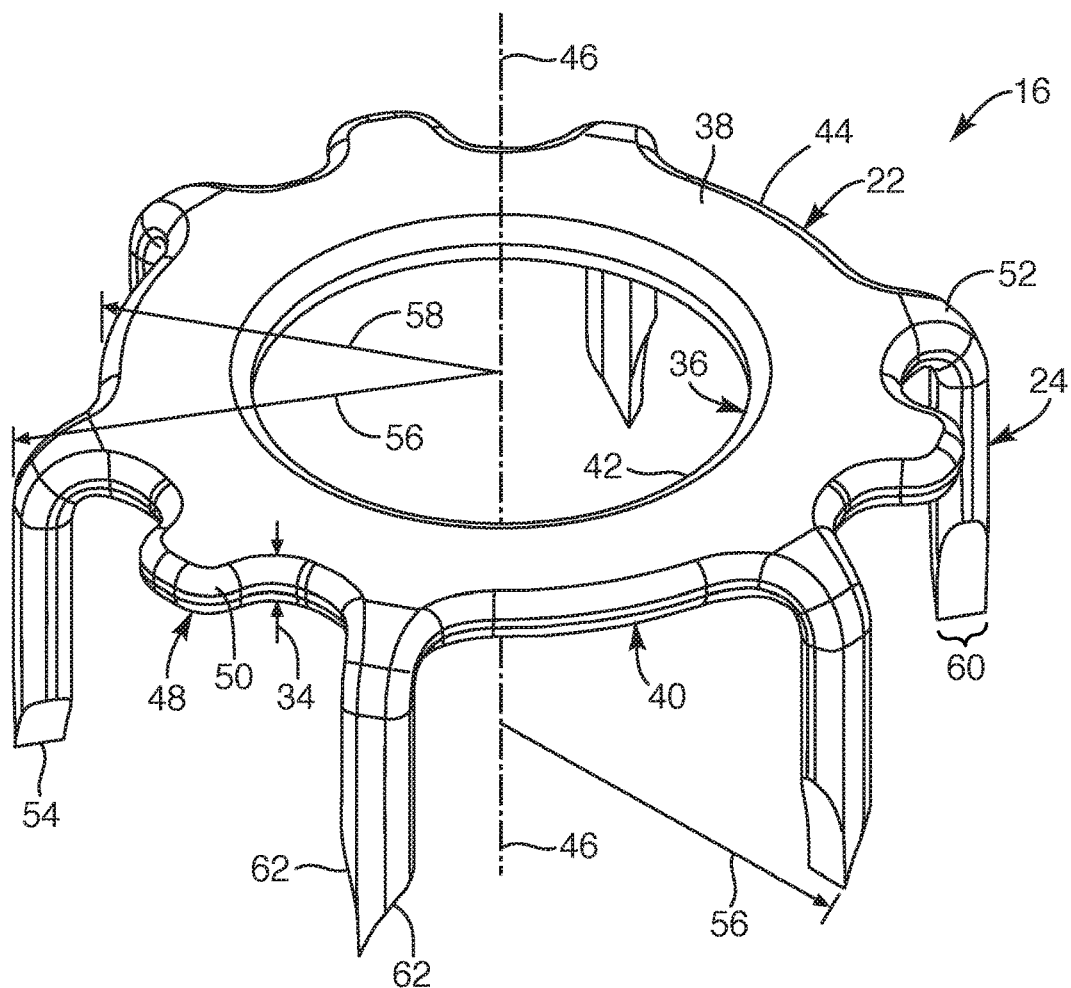
FIG. 2 is a perspective view of a soft tissue anchor, according to another embodiment of the present invention.
Figure 2A:
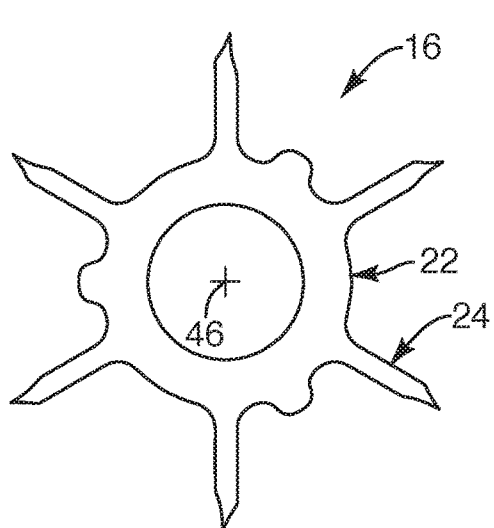
FIG. 2A is a top view of the soft tissue anchor of FIG. 2, depicting the soft tissue anchor as cut from sheet material, according to another embodiment of the present invention.
Figure 2B:
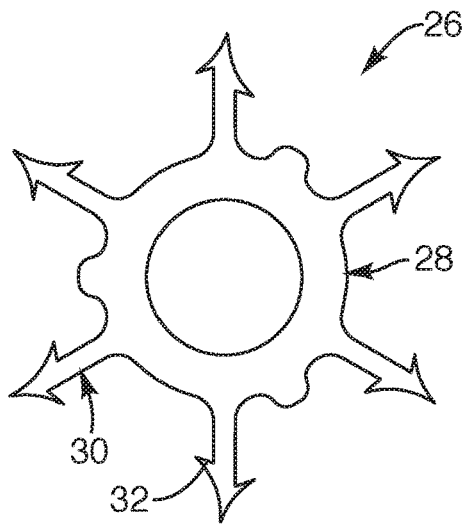
FIG. 2B is a top view of a soft tissue anchor, depicting another embodiment of the soft tissue anchor as cut from sheet material, according to the present invention.

Now with reference to FIGS. 2 and 2A, the soft tissue anchor 16 will now be described. As set forth, the soft tissue anchor 16 may be sized and configured to sink into soft tissue and be coupled thereto. The soft tissue anchor 16 may include a base 22 and multiple legs 24 extending from the base 22. The soft tissue anchor 16 may be formed from sheet material so that the anchor 16, including the base 22 and the multiple legs 24, may be formed as a seamless, monolithic and one-piece structure, as depicted in FIG. 2A. The soft tissue anchor 16 may be formed from a metallic material, such as stainless steel, titanium, or Nitinol, or any other suitable medical grade material or combinations of materials. Such metallic material may be laser cut from the sheet material or cut using any suitable technique known in the art. In another embodiment, the soft tissue anchor 16 may be formed from a polymeric material or a bioresorbable material. Upon being cut from the sheet material, the legs may be bent to position the legs downward or moved to orient the legs to extend away from a single side or underside of the anchor 16, as depicted in FIG. 2. Once the legs 30 have been appropriately oriented and bent into position, the anchor may then be electro polished or chemically polished, as desired. In another embodiment, the soft tissue anchor 16 may be formed from a medical grade polymeric material, as known to one of ordinary skill in the art. In another embodiment, the soft tissue anchor 16 may be formed from a bioresorbable material, as known to one of ordinary skill in the art. In another embodiment, as depicted in FIG. 2B, a soft tissue anchor 26 may include a base 28 with legs 30 extending therefrom such that the legs 30 may be formed with a barb 32 or multiple barbs extending therefrom. Such soft tissue anchor 26 may be formed in a similar manner as the soft tissue anchor described and depicted relative to FIGS. 2 and 2A herein and may be employed with the medical device system 10 (FIG. 1) as described and depicted herein.

With reference to FIG. 2, the base 22 of the soft tissue anchor 16 may be flat and generally include a thickness 34 of the before-discussed sheet material. The base 22 may extend in a generally circular configuration with a central opening 36 defined therein so as to define a flat ring like structure or the like. With such central opening 36, the base 22 may define an upper surface 38 and an underside surface 40 each extending to an inner periphery 42 and an outer periphery 44 of the base 22. The central opening 36 may be centered axially so as to define a tissue anchor axis 46 (see also FIG. 2A) extending perpendicular relative to the upper surface 38 and underside surface 40 of the base 22. Further, the upper surface 38 and the underside surface 40 may extend, for the most part, in a planar manner such that the base 22 extends as a flat structure. In another embodiment, the upper surface 38 and/or the underside surface 40 may be formed with a dome configuration.

In one embodiment, the anchor 16 may include coupling structure 48 sized and configured to couple the one or more flexible members 20 thereto. Such coupling structure 48 may be formed on or in the base 22 so as to be associated with the outer periphery 44 or the inner periphery 42 or both. For example, the base 22 may include the coupling structure 48 that may be in the form of multiple extensions or protrusions 50 extending outward from the base 22 so as to expand the surface area of the upper surface 38 and underside surface 40 of the base 22. Further, for example, the outer periphery 44 may include three protrusions 50 such that each protrusion may extend along the outer periphery 44 between separate pairs of the multiple legs 24. In another embodiment, the coupling structure 48 may be in the form of notches or recesses formed in the outer periphery or through holes extending between the upper surface 38 and the underside surface 40 of the base 22. In another embodiment, the coupling structure 48, similar to that described, may extend from or be defined in the inner periphery 42 of the base 22. In another embodiment, the above-described coupling structure 48 may extend from or be defined in both the inner and outer peripheries 42, 44 of the base 22 or the like. In still another embodiment, one or more of the legs 24 may act, at least in part, as the coupling structure 48 for coupling the one or more flexible members 20.

As previously set forth, the soft tissue anchor 16 may include the multiple legs 24 that may extend from the base 22. For example, the soft tissue anchor 16 may include six legs or more or less legs. In some applications, it may only be necessary for the soft tissue anchor 16 to include three, four, or five legs. In other applications where the holding strength needs to be greater, the soft tissue anchor 16 may include seven or eight legs. In another embodiment, the multiple legs 24 may extend from the outer periphery 44 so as to bend downward. In one embodiment, the multiple legs 24 may extend in a common direction. In another embodiment, the legs 24 may extend downward so as to be oriented to extend generally from the underside surface 40 of the base 22. In another embodiment, the legs 24 may extend substantially perpendicular relative to the underside surface 40 and substantially parallel relative to the tissue anchor axis 46. In another embodiment, each of the legs 24 may extend from the base 22 with a curvature 52 or a radius from the outer periphery 44 to then extend generally linear to a free end 54. With such curvature 52 or radius, the legs 24 may extend downward relative to the base 22 such that the free end 54 of the legs 24 may be positioned with a radial distance 56 relative to the tissue anchor axis 46 that may be larger than a radial distance 58 of the outer periphery 44 relative to the tissue anchor axis 46. Some portions of the outer periphery 44, such as ends of the protrusions 50, may extend further radially or include a similar radial distance relative to the tissue anchor axis 46 as the radial distance 56 of the legs 24 or free ends 54 of the legs. Further, the free end 54 of each leg 24 may extend with a free edge 60 such that an end portion of each leg may extend with a tapered portion 62 sized and configured to taper to the free end 54. Such free edge 60 may be defined by the thickness 34 of the sheet material and may be pointed so as to facilitate the legs 24 of the anchor 16 to readily penetrate soft tissue.

Now with reference to FIG. 3, the repair device system 14, in an assembled state, and the components thereof will now be described. As previously set forth, the repair device system 14 may include the soft tissue anchor 16 associated with or coupled to the bone anchor 18. The bone anchor 18 may be sized and configured to be permanently seated within a pre-formed hole (not shown). The bone anchor 18 may be formed of a polymeric material, such as PEEK (polyether ether ketone), or any other suitable polymeric material. In another embodiment, the bone anchor 18 may be formed of a metallic material, such as titanium, or any other suitable metallic material or combination of metallic materials, such as stainless steel. In still another embodiment, the bone anchor 18 may be formed of a bioresorbable material, such as PLGA (polylactic-co-glycolic acid), or any other suitable bioresorbable material. Further, such bone anchor 18 may be formed using typical manufacturing processes, as known to one of ordinary skill in the art.

In one embodiment, the bone anchor 18 may be an elongated structure 70 to define a bone anchor axis 72, the bone anchor axis 72 extending axially and centrally relative to the elongated structure 70. The elongated structure 70 of the bone anchor 18 may extend between a proximal end 74 and a distal end 76. In one embodiment, the bone anchor 18 may be sized and configured with structure to couple to the before-described soft tissue anchor 16. In another embodiment, the bone anchor 18 may include bone coupling structure 78 sized and configured to couple to bone. For example, the bone coupling structure 78 may include multiple ribs 80 along an outer surface 82 of the bone anchor 18. The multiple ribs 80 may extend laterally relative to the elongated structure 70 of the bone anchor 18. Each of the multiple ribs 80 may extend continuously around the outer surface 82 of the bone anchor 18 such that the ribs 80 may each exhibit a laterally extending arcuate structure. Further, each of the multiple ribs 80 may be evenly spaced relative to each other. Further, each rib 80 may each extend to define a proximal rib shelf 84 and a descending tapering side wall 86, tapering downward from the proximal rib shelf 84, such that the side wall 86 may extend downward to the proximal rib shelf 84 of a distal rib. In another embodiment, the bone coupling structure 78 may include winding threads extending along the outer surface 82 of the bone anchor 18.

The proximal end 74 of the bone anchor 18 may include a proximal end surface 88 that may define a generally circular profile. Further, the proximal end surface 88 may define a proximal end hole 90 or recess that may receive an engaging structure 142 (FIG. 1) of the delivery instrument 12, discussed further herein. Such proximal end hole 90 may be centrally aligned along the bone anchor axis 72 and within the proximal end surface 88. Further, the proximal end hole 90 may be defined with a downward or distally extending side wall 92 or side walls. In one embodiment, the distally extending side wall 92 may slightly taper inward toward the bone anchor axis 72 so as to facilitate an interference fit of the engaging structure 142 (FIG. 1) of delivery instrument 12 sized and configured to be inserted in the proximal end hole 90. In another embodiment, the engaging structure 142 may slightly taper toward a distal end 122 of the delivery instrument 12 (see FIG. 1).

The distal end 76 or distal end portion of the bone anchor 18 may define a notch 94 or recess therein. Such notch 94 may be sized and configured to receive a portion of one of the one or more flexible members 20. The notch 94 may be an opening extending as a channel in the distal end 76 of the bone anchor 18 such that the notch 94 may extend within the distal end portion of the bone anchor 18 so that a portion of the notch 94 extends through opposing sides 96 of the distal end portion of the bone anchor 18. In this manner, the notch 94 adjacent the distal end 76 of the bone anchor 18 may receive one of the one or more flexible members 20 to then be pulled deeper within the notch 94 so that the flexible member 20 may extend through and from the opposing sides 96 of the notch 94 adjacent the distal end portion of the bone anchor 18.

As previously set forth, the soft tissue anchor 16 may be coupled to the bone anchor 18 with the one or more flexible members 20. The one or more flexible members 20 may be formed from one or more polymeric filaments or fibers. The polymeric filaments or fibers may be a polyethylene material, such as ultra-high-molecular-weight polyethylene ("UHMWPE"), a polyester material, a polypropylene material, or the like. In another embodiment, the one or more flexible members 20 may be formed of suture material. In another embodiment, the polymeric filament or fiber may be a bioresorbable material, such as polylactide ("PLA"), polycaprolactone ("PCL"), polydioxanone ("PDX"), or the like, or any other suitable bioresorbable material as known to one of ordinary skill in the art. In another embodiment, the filaments or fibers may be formed in a woven or braided configuration or may extend with strands wound in a side-by-side configuration, or may extend with strands wound side-by-side and in a twisted configuration or any other suitable configuration to form a flexible member.

In one embodiment, the one or more flexible members 20 may include a first flexible member 98 and a second flexible member 100. The first flexible member 98 may extend with a continuous loop. The continuous loop of the first flexible member may be sized and configured to extend around the coupling structure 48 of the base 22, such as the protrusions 50, so that the continuous loop wraps around the base 22 of the soft tissue anchor 16. The continuous loop of the first flexible member 98 may extend with filaments in a braided or woven configuration. In another embodiment, the first flexible member may be a flexible wrap made of one or more flexible filaments that may be wound around the coupling structure 48 of the base 22, such as the protrusions 50, such that the one or more flexible filaments may be wound with multiple windings.

The second flexible member 100 may extend with a continuous loop. In another embodiment, the second flexible member 100 may extend with a loop with two free ends. In another embodiment, the second flexible member 100 may be a suture or the like. The second flexible member 100 may extend to wrap around and couple to the first flexible member 98 adjacent the base 22 of the soft tissue anchor 16. Further, the second flexible member 100 may couple to the first flexible member 98 at multiple locations, such as three locations along the first flexible member 98. For example, the second flexible member 100 may wrap over and couple to mid-portions 102 between connection points 104 of the first flexible member 98 and the protrusions 50 of the base 22 such that the second flexible member 100 may pull the mid-portions 102 inward relative to the base 22 and over the central opening 36 adjacent the inner periphery 42 of the base 22. From the mid-portions 102 of the first flexible member 98, the second flexible member 100 may extend downward through the central opening 36 of the soft tissue anchor 16 with a descending flexible member portion that may be in the form of a descending loop portion 106. The descending loop portion 106 may include a lower loop portion 108 that may be coupled to the bone anchor 18. In one embodiment, the lower loop portion 108 of the descending loop portion 106 may be inserted into the notch 94 defined in the bone anchor 18 to couple the soft tissue anchor 16 to the bone anchor 18, as previously described. The descending loop portion 106, descending from the first flexible member 98, may extend downward with a predetermined length 110 so that the bone anchor 18 may be positioned a predetermined distance from the soft tissue anchor 16. In this manner, the repair device system 14 may be assembled with the one or more flexible members 20, such as the first and second flexible members 98, 100, coupling the soft tissue anchor 16 to the bone anchor 18. Further, in this manner, the soft tissue anchor 16 may maintain a substantially fixed distance from the bone anchor 18 upon the one or more flexible members 20 being pulled taut. Further, the soft tissue anchor 16 may be coupled to the bone anchor 18 with the one or more flexible members 20 such that the tissue anchor axis 46 and the bone anchor axis 72 may be substantially coaxial or substantially parallel relative to each other.

Figure 3:
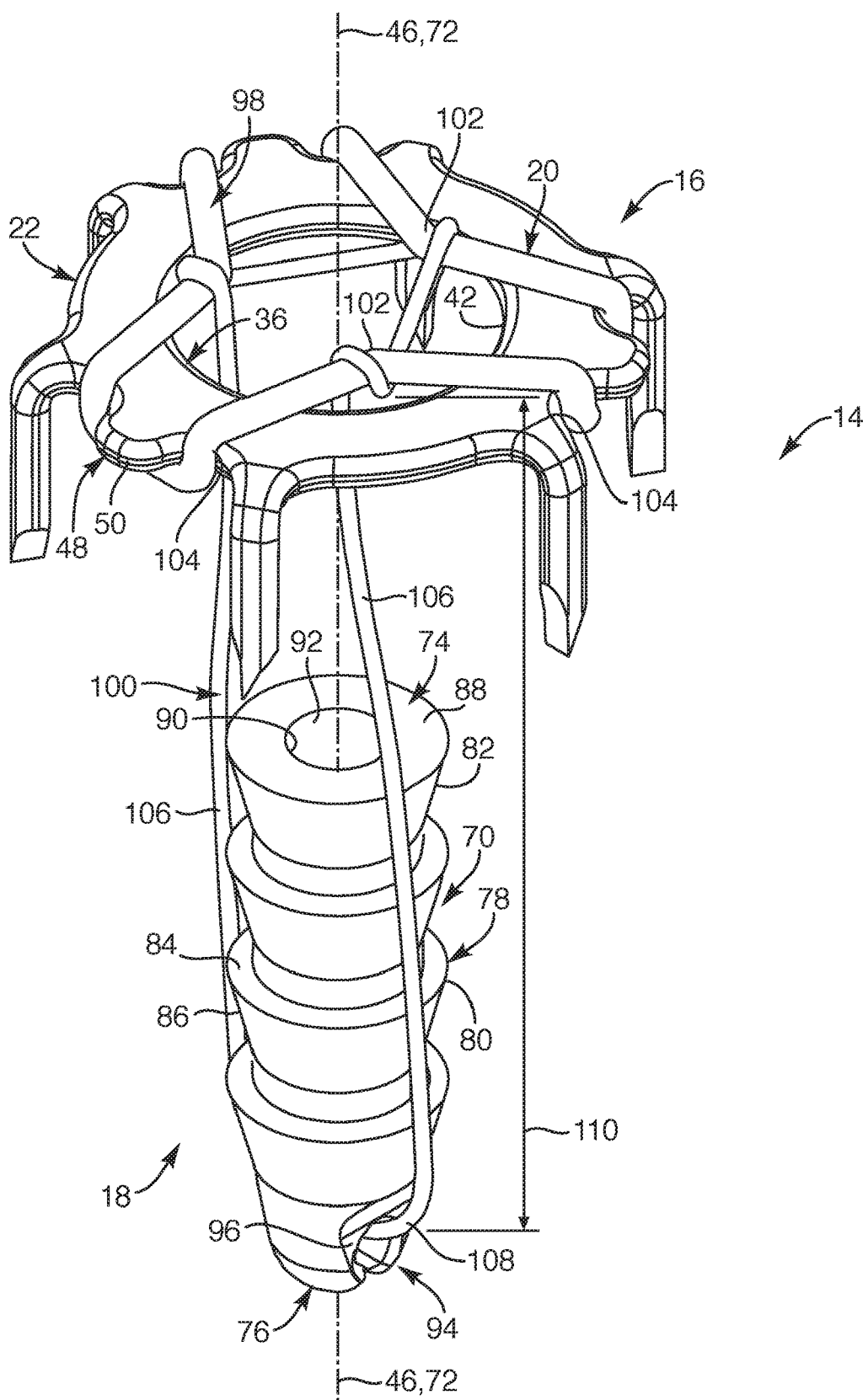
FIG. 3 is a perspective view of the repair device system of FIG. 1, depicting a bone anchor coupled to the soft tissue anchor with one or more flexible members, according to another embodiment of the present invention.
Figure 3A:
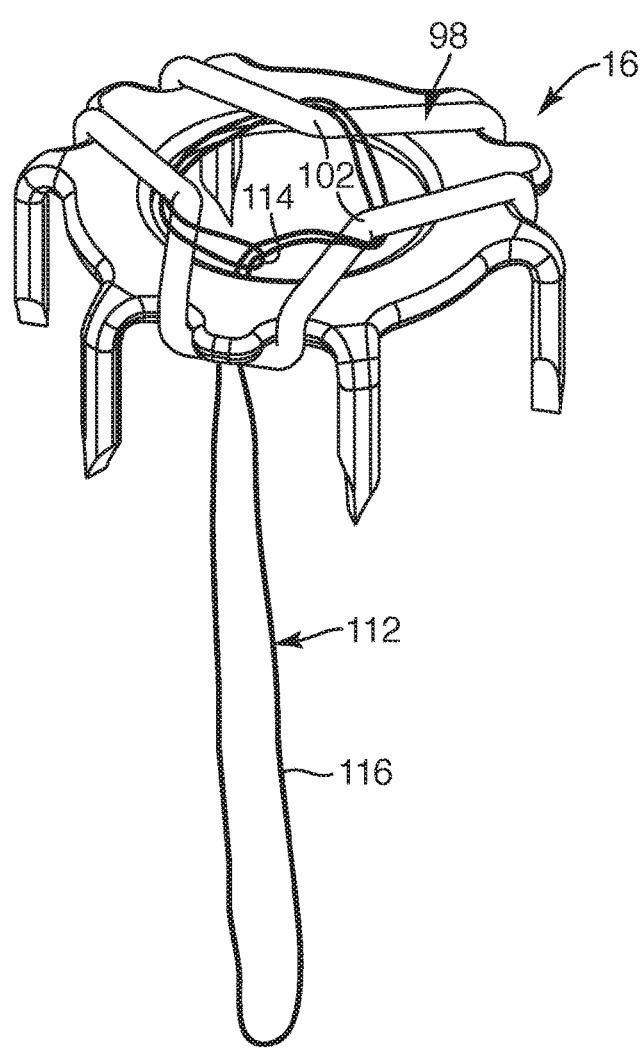
FIG. 3A is a perspective view of the soft tissue anchor, depicting another embodiment of the one or more flexible members coupled to the soft tissue anchor, according to the present invention.

With respect to FIG. 3A, another embodiment of a second flexible member 112 extending in continuous loop form is provided. In this embodiment, the second flexible member 112 may be coupled to the first flexible member 98 and to the soft tissue anchor 16 in a similar manner previously described. The second flexible member 112 in this embodiment may loop around the mid-portions 102 of the first flexible member 98 such that the continuous loop may be passed through itself at one loop end portion 114 to then extend downward with a descending loop portion 116 which may be sized and configured to couple to the bone anchor 18 (FIG. 3), similar to that previously described.

Figure 4:
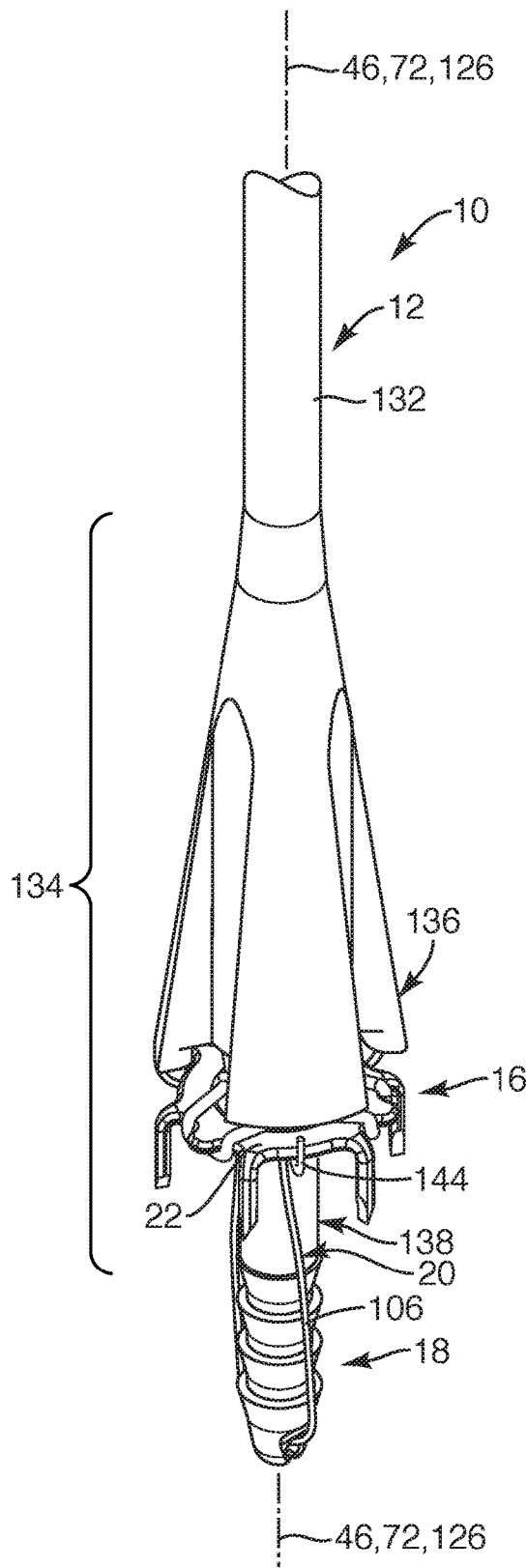
FIG. 4 is a partial perspective view of the medical device system of FIG. 1, depicting the medical device system in assembled form prior to delivery of the repair device system, according to another embodiment of the present invention.

With the repair device system 14 assembled, as depicted in FIG. 3, the assembled repair device system may be assembled with the delivery instrument 12, as depicted in FIG. 4. Now with reference to FIGS. 1, 3, 4 and 5, the delivery instrument 12 and assembly with the repair device system 14 will now be described.

The delivery instrument 12 may be an elongated structure extending between a proximal end 120 and a distal end 122 with a longitudinal length 124. The delivery instrument 12 may define a delivery instrument axis 126 extending centrally along the length 124 of the delivery instrument 12. The proximal end 120 may define a proximal impact surface 128 positioned proximally of a handle 130. The delivery instrument 12 may also include an impact shaft 132 coupled to the handle 130 and extending longitudinally and distally from the handle 130 along the delivery instrument axis 126. Further, the delivery instrument 12 may include a distal end portion 134, the distal end portion 134 including a clipping portion 136, an alignment portion 138, a distal impact surface 140, and engaging structure 142. The clipping portion 136 may be coupled to a distal portion of the impact shaft 132 and may include one or more clips 144 for suspending the soft tissue anchor 16 adjacent a distal underside of the clipping portion 136. The alignment portion 138 may extend distally of the clipping portion 136 with a cylindrical structure and may be a continuous extension of the impact shaft 132. The engaging structure 142 may extend distally of the alignment portion 138 and, more specifically, may extend from and distal of the distal impact surface 140. The distal impact surface 140 may be defined as a shelf 146 extending laterally from the engaging structure 142 and may extend substantially perpendicular relative to the delivery instrument axis 126. The engaging structure 142 may be cylindrical or the like and may be sized and configured to mate and correspond with the proximal end hole 90 of the bone anchor 18 so that the distal impact surface 140 abuts against the proximal end surface 88 of the bone anchor 18. With this arrangement, the distal end portion 134 of the delivery instrument 12 may be removably coupled to the repair device system 14, as described below.

With the repair device system 14 assembled, the alignment portion 138 of the delivery instrument 12 may be inserted through the central opening 36 of the soft tissue anchor 16 to then position the engaging structure 142 into the proximal end hole 90 of the bone anchor 18. The one or more clips 144 may be positioned along the underside surface of the base 22 of the soft tissue anchor 16 to suspend the soft tissue anchor 16 below an underside of the clipping portion 136. In this position, the one or more flexible members 20 including the descending loop portion 106 may be placed in a somewhat taut orientation or position. With the repair device system 14 coupled to the distal end portion 134 of the delivery instrument 12, each of tissue anchor axis 46, the bone anchor axis 72 and the delivery instrument axis 126 may be coaxial or substantially coaxial relative to each other. Further, with this arrangement, the repair device system 14 may be removably coupled to the distal end portion 134 of the delivery instrument 12 and may be employed to fixate soft tissue 5 to bone 7.

Figure 5:
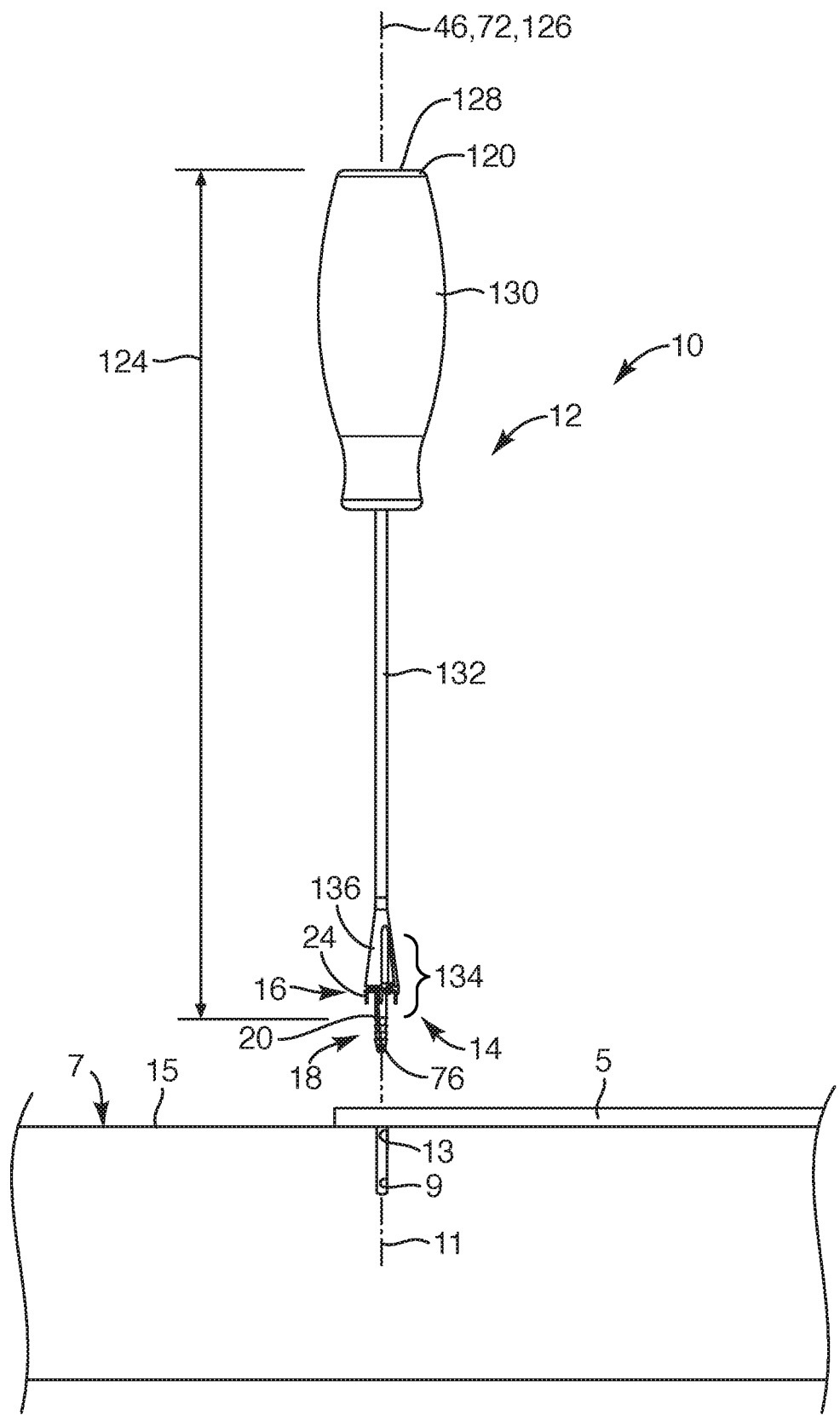
FIG. 5 is a side view of the medical device system, depicting the system prior to being delivered to a pre-formed hole in bone and fixating soft tissue to the bone, according to another embodiment of the present invention.

Now with reference to FIGS. 5 and 6, an embodiment for delivering the repair device system 14 with the delivery instrument 12 will now be described. In preparation to deliver the repair device system 14, a physician may form a hole 9 in the bone 7 adjacent to the location desired for fixating the soft tissue 5. Such hole 9 in the bone 7 may be prepared with a suitably sized awl (not shown) or the like, as known to one of ordinary skill in the art. The depth of the hole 9 may be deeper than a height or elongated length of the bone anchor 18 and should be sized and configured to receive the bone anchor 18 with an interference fit such that the ribs 80 of the bone anchor 18 stabilize and appropriately seat the bone anchor 18 in the bone 7. Once an appropriate hole 9 has been pre-formed in the bone 7, the physician may position a portion of the soft tissue 5 desired for fixating to the bone 7 to a position over the pre-formed hole 9 in the bone 7. The physician may then form a thin slit (not shown), such as with a scalpel, within the soft tissue 5 directly above the pre-formed hole 9 in the bone 7. The distal end 76 of the bone anchor 18, being assembled with the delivery instrument 12, may then be positioned and inserted through the slit in the soft tissue 5 so that the distal end 76 is positioned within a top portion 13 of the pre-formed hole 9 in the bone 7. The physician may then orient the delivery instrument 12 so that the delivery instrument 12 may be substantially aligned and coaxial with a central axis 11 of the pre-formed hole 9. At this juncture, the physician may employ an impacting instrument, such as a hammer (not shown), to impact the proximal impact surface 128 of the delivery instrument 12. The impact force of the hammer directly translates to an impact force placed upon the proximal end surface 88 of the bone anchor 18 abutted with the distal impact surface 140 of the delivery instrument 12 (see FIGS. 1 and 3). As the physician continues to hammer the proximal impact surface 128 of the delivery instrument 12, the bone anchor 18 may be driven into the pre-formed hole 9 to a depth desired by the physician. Further, as the bone anchor 18 is driven deeper into the pre-formed hole 9, the legs 24 of the soft tissue anchor 16 may simultaneously be driven into the soft tissue 5.

Upon the bone anchor 18 being seated or prior to being fully seated, the one or more clips 144 (FIG. 4) holding the soft tissue anchor 16 against the clipping portion 136 may be removed. As the physician continues to seat the bone anchor 18 into the pre-formed hole 9 to a depth below an outer surface 15 of the bone 7, the soft tissue 5 becomes clamped with a clamping force 150 against the outer surface 15 of the bone 7 with the soft tissue anchor 16 being forced downward as the bone anchor 18 is impacted downward due to the fixed length of the one or more flexible members 20 (and predetermined length 110 (FIG. 3) of the descending loop portion 106), which results in a fixed distance between the bone anchor 18 and the soft tissue anchor 16. Due to variableness of the thickness of soft tissue 5 that may be encountered, the physician may gauge the clamping force 150 or tightness of the soft tissue 5 against the bone 7 by continuing to drive the bone anchor 18 into the bone until the soft tissue 5 is clamped against the bone 7 with an appropriate clamping force. In this manner, the repair device system 14 may be employed with various thicknesses of soft tissue 5.

Further, the repair device system 14 provides advantages for physicians by eliminating complex suture patterns necessitated for threading and cinching the soft tissue against bone and implanted bone anchors, whereas the repair device system 14 of the present invention, upon appropriately seating the bone anchor 18 in the bone 7, the soft tissue 5 simultaneously becomes fixated to the bone with the soft tissue anchor 16. Further, the repair device system 14 minimizes potential issues by being implantable in a centralized manner without tangential components and sutures being coupled at non-centralized locations, thereby eliminating complexity and potential irritation due to multiple non-centralized components.

Figure 6:
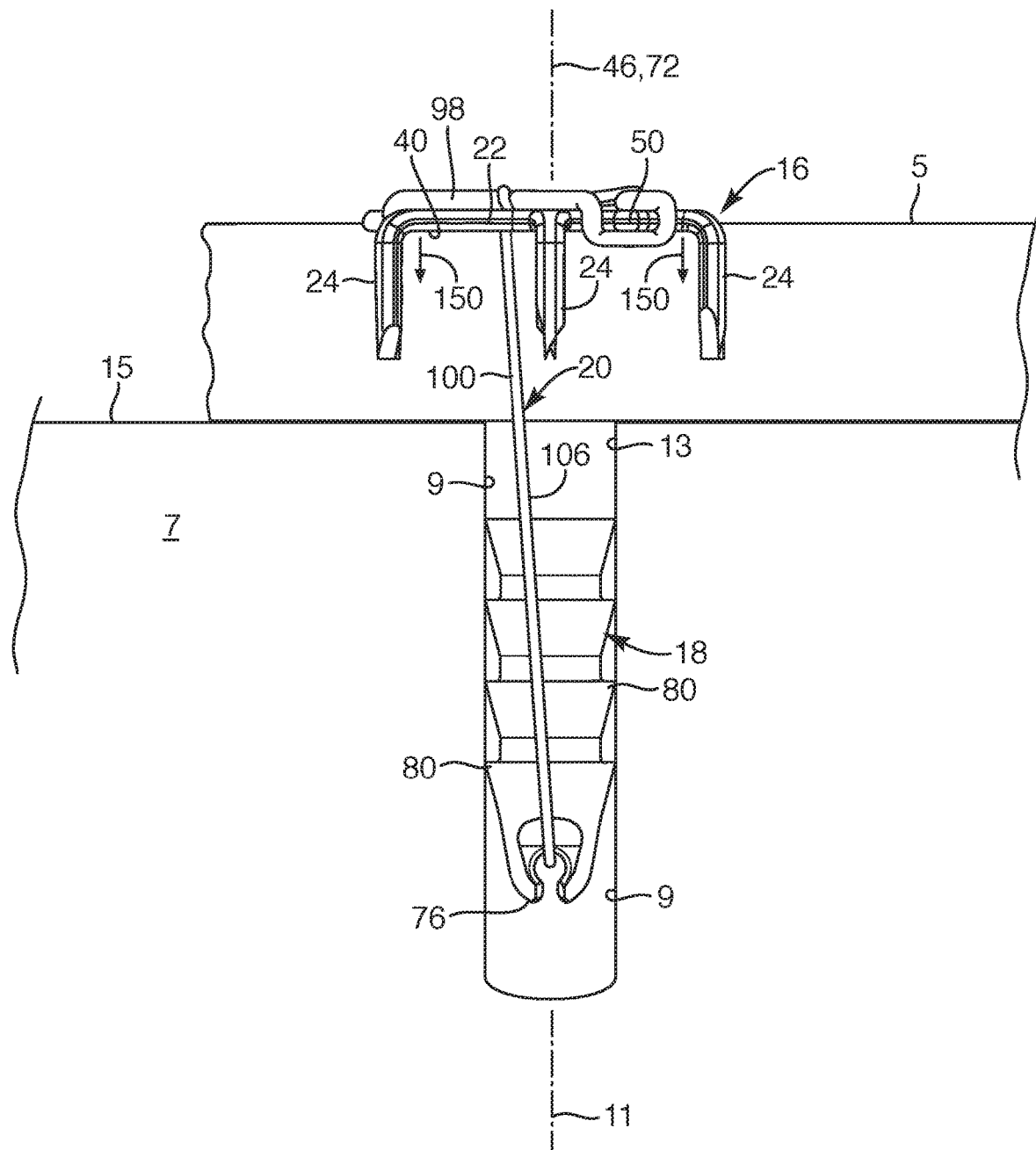
FIG. 6 is a side view of the repair device system, depicting the bone anchor implanted in bone and the soft tissue anchor holding the soft tissue against the bone in a fixated manner, according to another embodiment of the present invention.

Further, with reference to FIGS. 3 and 6, the coupling of the second flexible member 100 to the first flexible member 98 facilitates multiple attachment points adjacent the inner periphery 42 of the base 22 of the soft tissue anchor 16, thereby, more effectively distributing the clamping force 150 across the underside surface 40 of the base 22 of the soft tissue anchor 16 against the soft tissue 5. Even further, such distribution of the clamping force 150 by the coupling of the one or more flexible members 20 along multiple attachment points around the protrusions 50 of the base 22 and between the first and second flexible members 98, 100 at the mid portions 102 minimizes the potential for failure of the first and second flexible members 98, 100. Furthermore, upon the soft tissue 5 becoming loaded laterally relative to the axes 46, 72 of the soft tissue anchor 16 and the bone anchor 18, the one or more flexible members 20 at their multiple attachment points adjacent the inner periphery 42 of the soft tissue anchor 16 may substantially minimize potential overloading due to a spring like effect at the attachment points between the first and second flexible members 98, 100 along the mid portions 102, thereby, minimizing potential failure at the repair site and minimizing potential lateral tearing of the legs 24 through the soft tissue 5. Also, during the healing process and thereafter, upon the soft tissue 5 becoming loaded by activity of the patient, the cooperation between the clamping force 150 of the soft tissue anchor 16 and the multiple legs 24 being seated within the soft tissue 5 may substantially prevent lateral movement of the soft tissue 5 relative to the bone 7, thereby, maintaining the soft tissue 5 to become properly fixated to the bone 7 and minimize failure and the potential for follow-up procedures. Also, upon fully healing, the only components exposed above the soft tissue may be the upper surface of the soft tissue anchor 16 and portions of the one or more flexible members 20 to provide an implant with a very low exposed profile, thereby, minimizing any potential long term irritation to the patient as well as minimizing potential irritation during the healing process.

Figure 7:
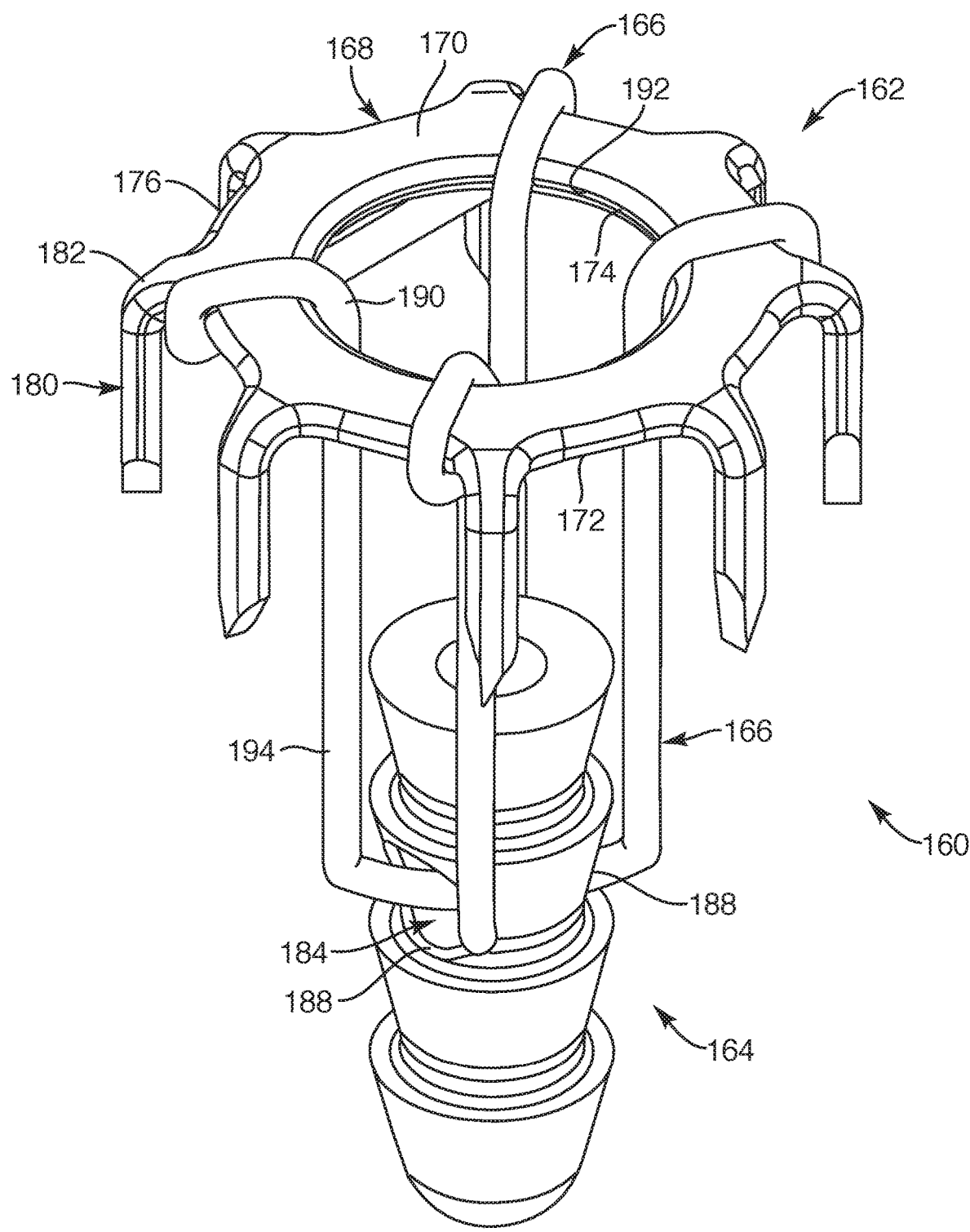
FIG. 7 is a perspective view of another embodiment of a repair device system, depicting one flexible member with the soft tissue anchor and the flexible member being coupled to an intermediate portion of the bone anchor, according to the present invention.

Now with reference to FIG. 7, another embodiment of a repair device system 160 is provided. This embodiment of the repair device system 160 may include similar structural characteristics and may be employed in a similar manner as the repair device system 14 of FIG. 3 and described in previous embodiments. This embodiment of the repair device system 160 may include a soft tissue anchor 162 coupled to a bone anchor 164 with one or more flexible members 166. The soft tissue anchor 162 may be similar to the soft tissue anchor of FIG. 2 and may include a base 168 with an upper surface 170 and an underside surface 172 extending between an inner periphery 174 and an outer periphery 176. In this embodiment, the base 168 may also include multiple legs 180, such as eight legs, each extending from the outer periphery 176 with a curvature 182 or radius and extending downward relative to the underside surface 172 of the base 168. Further, in this embodiment, the outer periphery 176 may not define the protrusions 50 depicted in FIG. 2 such that coupling structure may be the base 168 and portions of the legs 180. The bone anchor 164 may include similar structure of the bone anchor 18 described and depicted in FIG. 3, but in this embodiment, the bone anchor 164 may define an aperture 184 extending through an intermediate portion 186 of the bone anchor 164 such that the aperture 184 may extend to opposing sides 188 of the bone anchor 164.

Further, in this embodiment, the one or more flexible members 166 may extend with a single flexible member 190. Such single flexible member 190 may extend as a continuous loop or closed loop or may extend with two free ends. The single flexible member 190 may be one or more flexible filaments that may be woven together to form the single flexible member 190. The single flexible member 190 may be coupled to the base 168 and coupled against portions of the legs 180 of the soft tissue anchor 162. Further, the single flexible member 190 may extend from the base 168 and through a central opening 192 defined by the inner periphery 174 of the soft tissue anchor 162 so as to extend with a downward descending portion 194 to extend through the aperture 184 defined in the bone anchor 164. In this manner, the single flexible member 190 may be coupled to the bone anchor 164 and the soft tissue anchor 162. With this arrangement, the repair device system 160 may be coupled to bone and soft tissue for fixating the soft tissue to bone, similar to the repair device system 14 described and depicted in FIGS. 5 and 6.

Figure 8:
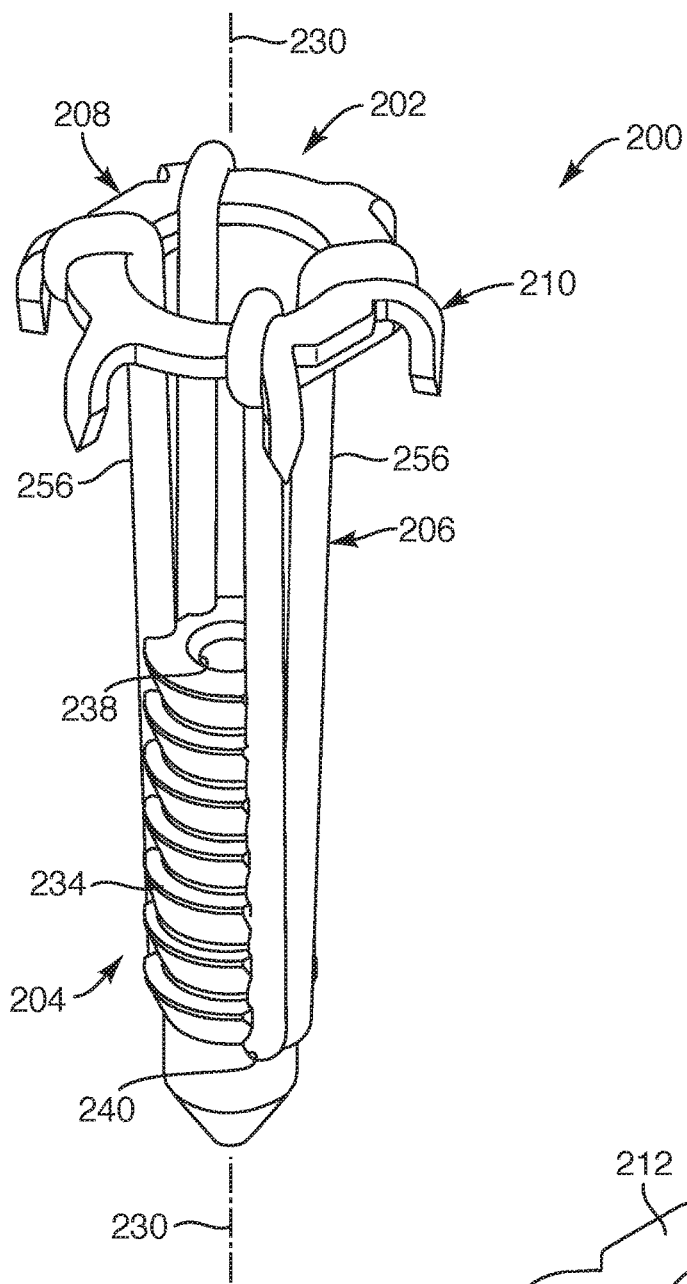
FIG. 8 is a perspective view of another embodiment of a repair device system, according to the present invention.
Figure 12:
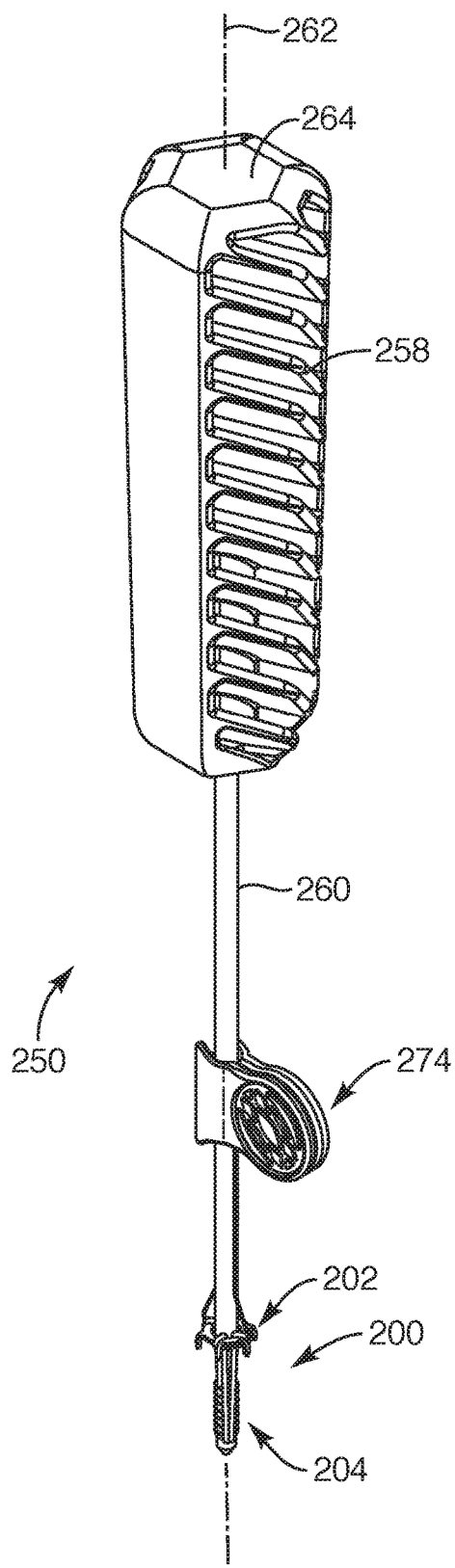
FIG. 12 is a perspective view of another embodiment of a medical device system, depicting a delivery instrument and the repair device system of FIG. 8, according to the present invention.

Now with reference to FIG. 8, another embodiment of a repair device system 200 that may be employed for fixating soft tissue to bone. This embodiment of the repair device system 200 may function similarly and include similar structure to the repair device systems depicted in previous embodiments. For example, the repair device system 200 may include a soft tissue anchor 202 interconnected to a bone anchor 204 with one or more flexible members 206. As in previous embodiments, the repair device system 200 may be employed with, for example, the delivery instrument 12 of FIG. 5 and may be employed for coupling soft tissue to bone in a similar manner and with similar functionality as depicted and described in FIGS. 5 and 6. Further, as will be apparent to one of ordinary skill in the art, the repair device system 200 of this embodiment may be employed with the delivery instrument 250, as depicted in FIG. 12, such that the repair device 200 and delivery instrument 250 may be employed with similar functionality for fixating soft tissue to bone as that described and depicted in FIGS. 5 and 6.

Figure 9:
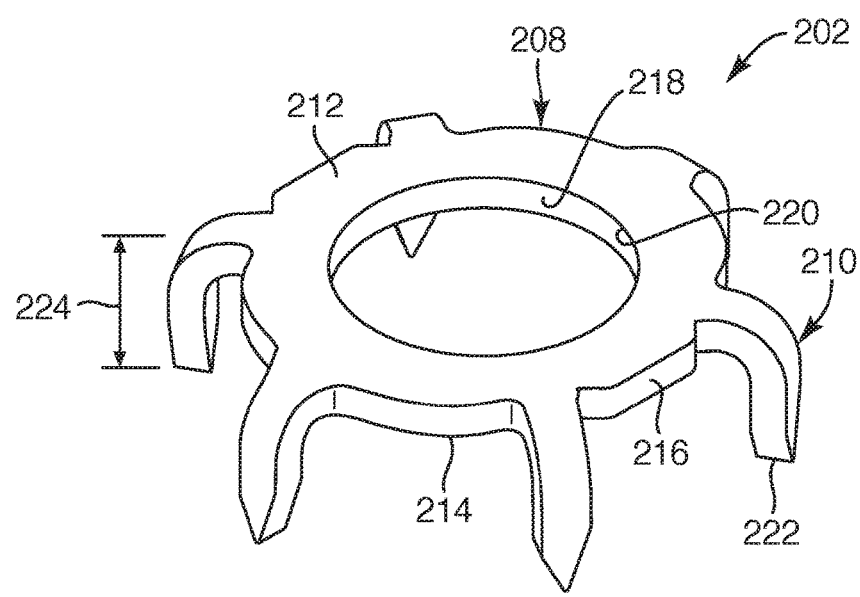
FIG. 9 is a perspective view of a soft tissue anchor of the repair device system of FIG. 8, according to another embodiment of the present invention.

With reference to FIGS. 8 and 9, the soft tissue anchor 202 may include a base 208 and multiple legs 210 that each may extend downward or in a substantially similar or common direction from the base 208. As in previous embodiments, the base 208 may exhibit a generally circular profile. The base 208 may exhibit a washer structure with the legs 210 or anchoring structure extending therefrom. The base 208 may include an upper surface 212 and an underside surface 214 each extending to and defining an outer periphery 216 and an inner periphery 218. The inner periphery 218 may define a central opening 220 or circular opening that may be symmetrically defined in the base 208. The legs 210 may extend directly from the outer periphery 216 such that the legs 210 may exhibit a bend or curve and then extend away from the underside surface 214. In one embodiment, the legs 210 may be elongated and extend generally perpendicular relative to the underside surface 214 of the base 208 along a majority of the elongated length of the legs. The legs 210 may extend to a distal end or free end 222 and may be sized and configured to sink into and engage with soft tissue. In one embodiment, the legs 210 may maintain a fixed configuration (pre-delivery and post-delivery into soft tissue) that may extend generally linearly, but for the above-described bend or curved portion of the legs 210 adjacent to the outer periphery 216 of the base 208. In one embodiment, similar to previous embodiments, the free end 222 or free end portion of the legs 210 may exhibit a straight edge profile (side view) and may also exhibit a point profile (front view). In another embodiment, each of the legs 210 may extend a similar length. The legs 210 of the soft tissue anchor 202 may be a length 224 sized and configured to extend with a partial depth into soft tissue, and not fully through the soft tissue. In one embodiment, the soft tissue anchor 202 may include six legs 210 or more, such as eight legs. In another embodiment, the soft tissue anchor 202 may include four legs, or at least four legs 210. In another embodiment, the soft tissue anchor 202 may include at least three legs 210.

Further, in another embodiment, the base 208 and legs 210 of the soft tissue anchor 202 may act as coupling structure for the flexible member 206. For example, the flexible member 206 may be coupled to two adjacent legs 210 as well as portions of the base 208, similar to that described and depicted in the embodiment of FIG. 7 and discussed in further detail herein. As such, in this embodiment, the outer periphery 216 of the base 208 of the soft tissue anchor 202 may extend with a circular profile, but for the legs 210, so as to not exhibit the protrusions as described in previous embodiments. With this arrangement, the flexible member 206 can effectively couple the soft tissue anchor 202 to the bone anchor 204.

Figure 10:
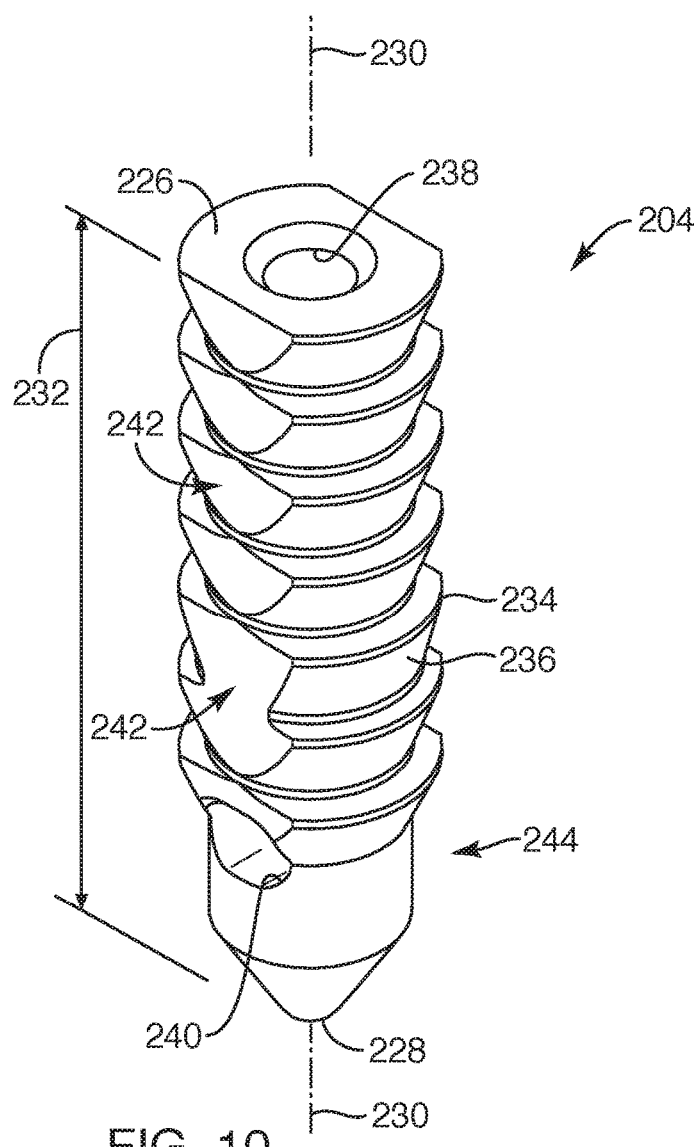
FIG. 10 is a perspective view of a bone anchor of the repair device system of FIG. 8, according to another embodiment of the present invention.
Figure 11:
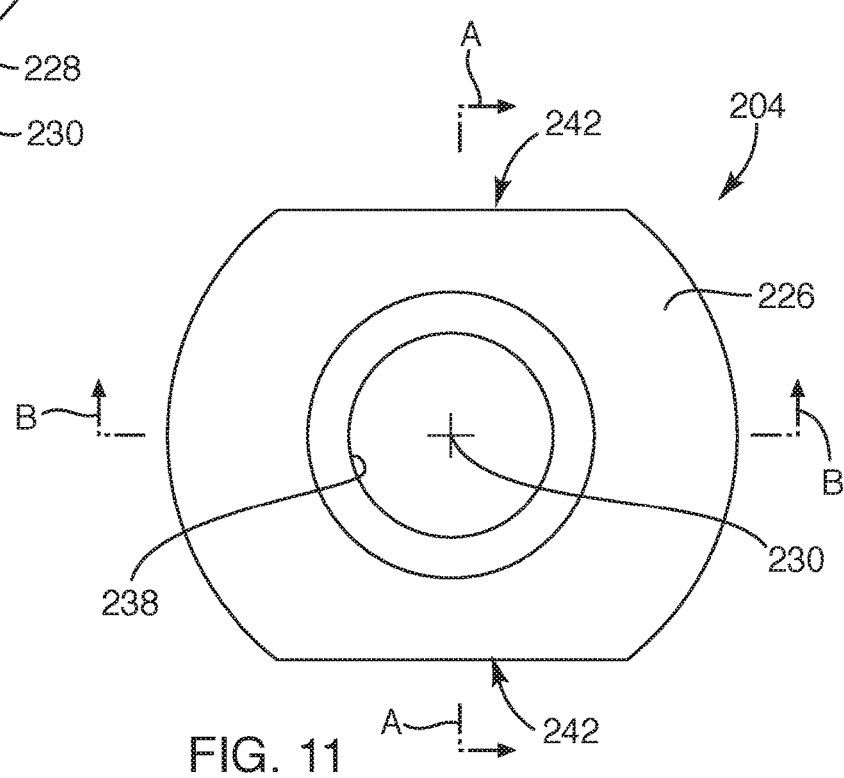
FIG. 11 is a top view of the bone anchor of FIG. 10, according to another embodiment of the present invention.

With reference to FIGS. 8, 10 and 11, the bone anchor 204 of the repair device system 200 will now be described. The bone anchor 204, similar to previous embodiments, may be an elongated structure extending between a proximal end 226 and a distal end 228 and defining a bone anchor axis 230 along a longitudinal length 232 of the bone anchor 204. Further, the bone anchor 204 may extend laterally with a circular profile (see FIG. 11) and may define ribs 234 extending radially along an external surface 236 of the bone anchor 204. Further, similar to previous embodiments, the bone anchor 204 may define a first hole 238 and a second hole 240 within the bone anchor 204. The first hole 238 may extend longitudinally along the bone anchor axis 230 and be defined in the surface along the proximal end 226 of the bone anchor 204. The second hole 240 may extend laterally relative to the bone anchor axis 230 and may extend between opposing sides of the bone anchor 204 adjacent the distal end 228 of the bone anchor 204 or at a location closer to the distal end 228 than the proximal end 226 of the bone anchor 204.

Figure 11A:
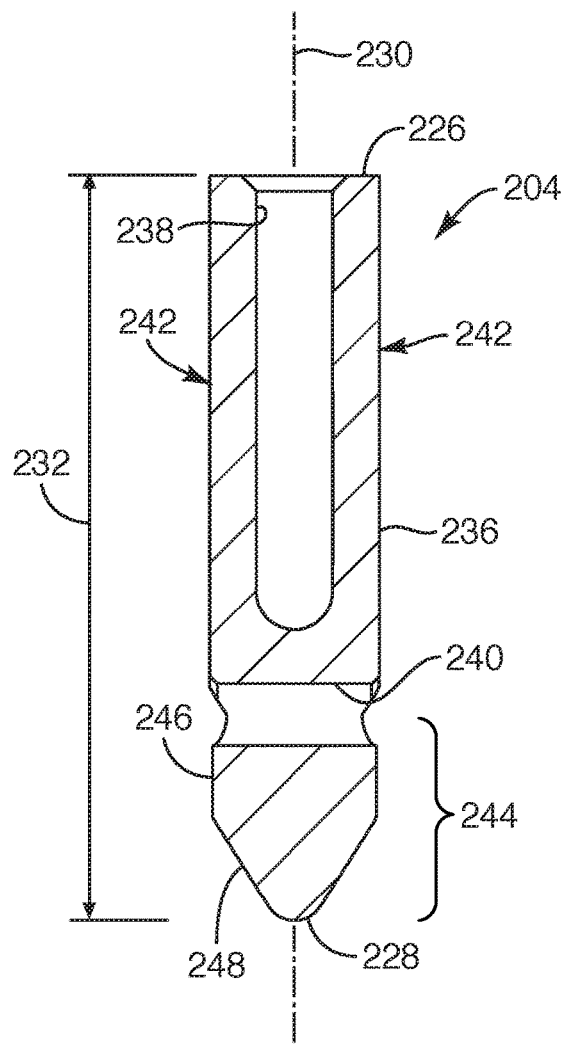
FIG. 11A is a cross-sectional view of the bone anchor taken along section line A-A of FIG. 11, according to another embodiment of the present invention.
Figure 11B:
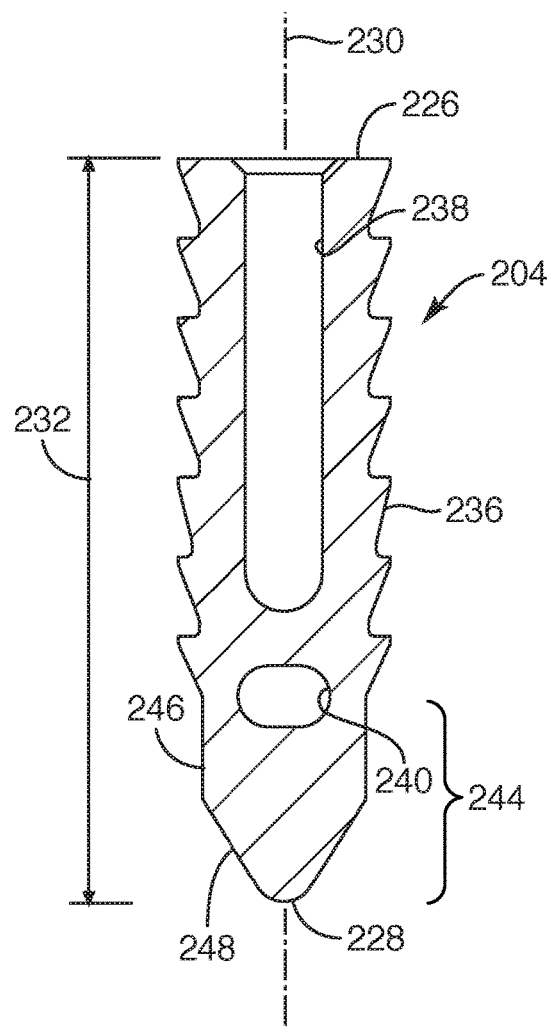
FIG. 11B is a cross-sectional view of the bone anchor taken along section line B-B of FIG. 11, according to another embodiment of the present invention.

Regarding FIGS. 10, 11A and 11B, the bone anchor 204 may include a flattened portion 242 or flattened side surface (see FIG. 11). Such flattened portion 242 may extend along opposing sides of the bone anchor so as to be at least partially defined in the ribs 234 along the external surface 236 of the bone anchor 204. Such flattened portion 242 may extend from the lateral second hole 240 to the proximal end 226 of the bone anchor 204. With such flattened portion 242, the flexible member 206 (FIG. 8) may extend through the lateral second hole 240 and extend upward along the opposing flattened portions 242 toward the soft tissue anchor 202 (see FIG. 8). With this arrangement, the ribs 234 may extend radially over the external surface 236 of the bone anchor 204 in a discontinuous manner so as to be separate and discrete relative to other ribs 234. Further, the external surface 236 of the bone anchor 204 may exhibit structure along a distal portion 244 of the bone anchor 204 to assist the bone anchor 204 to maintain proper orientation and alignment as the bone anchor 204 is implanted into bone. For example, the distal portion 244 of the bone anchor 204 may extend distally from the second hole 240 with a cylindrical surface 246 which may transition distally to a conical surface 248 so as to taper toward the distal end 228 of the bone anchor 204.

Further, as previously set forth, the bone anchor 204 may define the first and second holes 238, 240. The first hole 238 may be sized and configured to receive an engagement portion 252 of a delivery instrument 250 (see FIG. 13A) at the proximal end 226 of the bone anchor 204. The first hole 238 may extend within the bone anchor 204 in a deeper manner than depicted in previous embodiments so that the first hole 238 extends beyond a majority of the elongated length 232 of the bone anchor 204. As such, the first hole 238 may be sized to ensure appropriate engagement and to maintain alignment with the engagement portion 252 of the delivery instrument 250. The second hole 240 may extend laterally through and between opposing sides of the bone anchor 204 adjacent a lower end of the opposing flattened portions 242 of the bone anchor 204. Further, the second hole 240 may extend through the bone anchor 204 so as to extend symmetrically through the bone anchor axis 230. The second hole 240 may exhibit an oval profile, as shown in FIG. 11B, sized and configured to receive and hold the flexible member 206 (FIG. 8). In this manner, portions of the flexible member 206 may extend through the second hole in a side-by-side arrangement.

Now with reference to FIGS. 8, 12, 13 and 13A, the repair device system 200 may be removably coupled to a delivery instrument 250, similar to previous embodiments. As in previous embodiments, the soft tissue anchor 202 may be maintained in a coupled arrangement to the bone anchor 204 with one or more flexible members 206 and, as depicted in this embodiment, a single flexible member 206. For example, the flexible member 206 may extend through the laterally extending second hole 240 defined in the bone anchor 204 so that two opposing end loops 256 of the flexible member 206 may extend proximally along the opposing flattened portions 242 of the bone anchor 204. The end loops 256 may then be positioned through the central opening 220 of the soft tissue anchor 202 so that each end portion of the two end loops 256 may wrap around, for example, two adjacent legs 210 and portions of the base 208 of the soft tissue anchor 202. In this manner, the soft tissue anchor 202 may be coupled to the bone anchor 204 to form the repair device system 200.

Further, the repair device system 200 may be employed to fixate soft tissue to bone with the delivery instrument 250, similar to previous embodiments. For example, in this embodiment, the delivery instrument 250 may include a handle 258 and a shaft 260, the delivery instrument 250 defining a delivery instrument axis 262 extending longitudinally therein. The handle 258 may define a proximal end surface that may act as a proximal impacting surface 264 (for impacting with a hammer), similar to previous embodiments. The shaft 260 may be fixedly coupled to the handle 258 and may longitudinally extend distally to a distal end portion 266. The distal end portion 266 may include an alignment portion 268, an engagement portion 252, and a distal impacting surface 272. The alignment portion 268 may be sized and configured to be positioned through the central opening 220 of the soft tissue anchor 202. The engagement portion 252 may be sized and configured to be inserted through the first hole 238 defined in the proximal end 226 of the bone anchor 204 so that the distal impacting surface 272 of the delivery instrument 250 abuts with the proximal end 226 or proximal surface of the bone anchor 204. With this arrangement, the delivery instrument axis 262 may be coaxial with the bone anchor axis 230.

Figure 13:
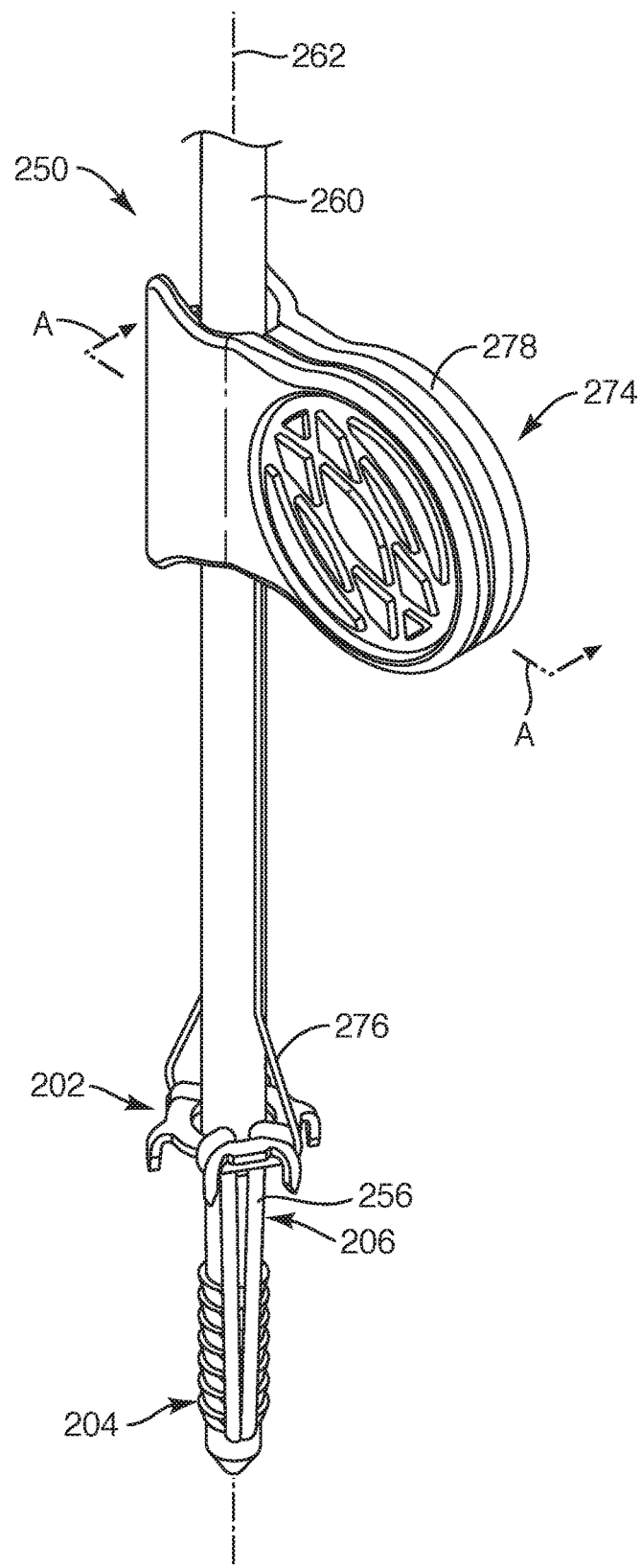
FIG. 13 is an enlarged view of the medical device system of FIG. 12, according to another embodiment of the present invention.
Figure 13A:
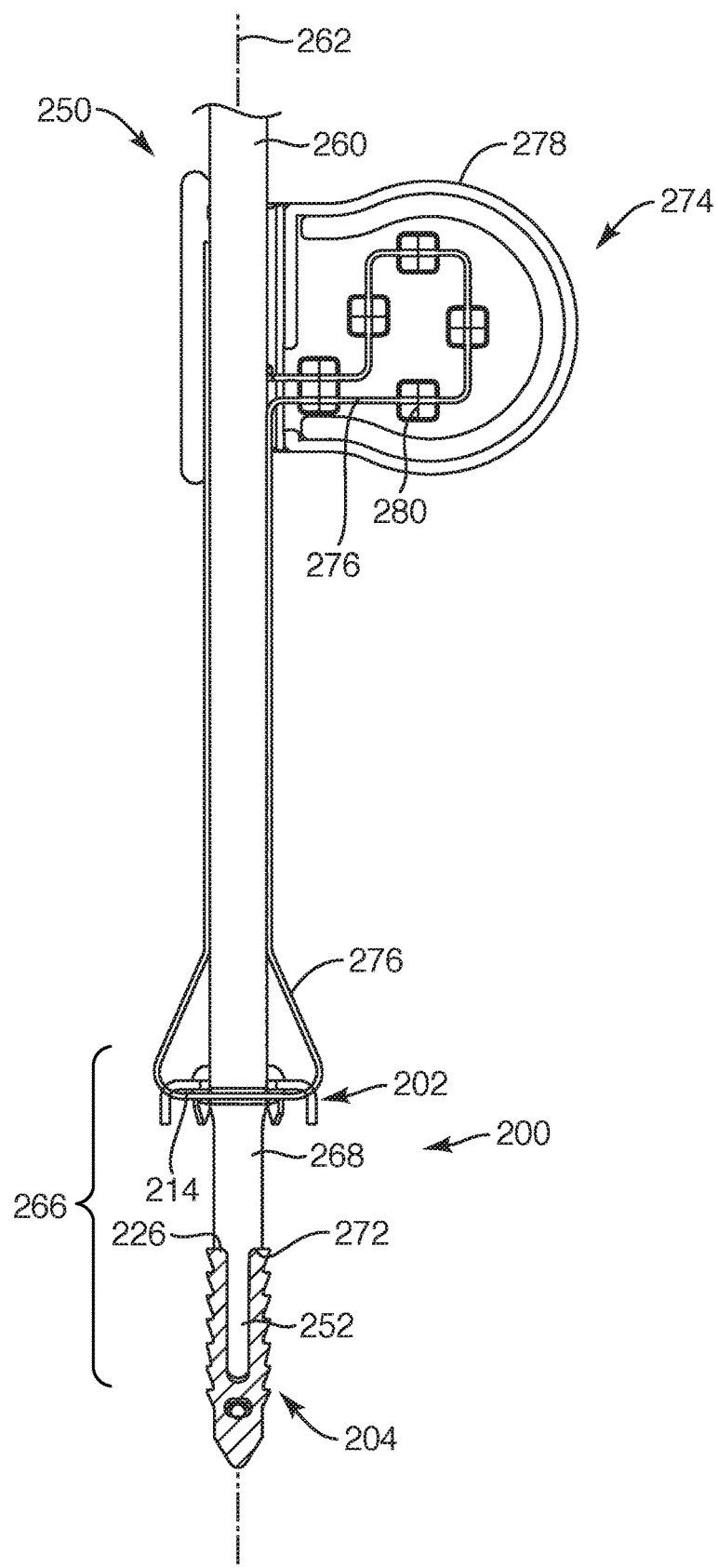
FIG. 13A is a cross-sectional view of the medical device system taken along section line A-A of FIG. 13, depicting a retainer element for holding the repair device system to the delivery instrument, according to another embodiment of the present invention.

In this embodiment, the repair device system 200 may be removably coupled to the delivery instrument 250 with a retainer element 274. With the distal end portion 266 of the delivery instrument 250 engaged with the bone anchor 204, as previously set forth, the retainer element 274 may be sized and configured to hold and suspend the soft tissue anchor 202 along the distal end portion 266 of the shaft 260 so that the flexible member 206 is taut or in a taut position. In this taut position, the soft tissue anchor 202 may be retained at and spaced a predetermined distance from the bone anchor 204 so as to be suspended above the bone anchor 204. The retainer element 274 may include a line 276 and a tab 278. The tab 278 may also be referenced as a retainer portion. As depicted in FIG. 13A, the line 276 may extend along the underside surface 214 of the base 208 of the soft tissue anchor 202 and extend upward on both sides of the base 208 to the tab 278. The tab 278 may define channels 280 therein or coupling structure for holding portions of the line 276. The tab 278 may also be sized to couple to the shaft 260 of the delivery instrument 250 with, for example, an interference fit or the like such that the line can be wrapped around the shaft 260 so as to assist in the interference fit. In this manner, the retainer element 274 may maintain the flexible member 206 in a taut position so as to temporarily and removably hold or couple the repair device system 200 to the delivery instrument 250 and, upon fixating soft tissue to bone with the repair device system 200, the line 276 may be removed by, for example, being snipped and then pulled from under the soft tissue anchor 202. In another embodiment, the tab 278 of the retainer element 274 may be removed from the shaft 260 to facilitate releasing the wrapped line 276 held between the tab 278 and the shaft 260 to, thereby, release the delivery instrument 250 from the repair device system 200.

Now with reference to FIGS. 14-15, another embodiment of a repair device system 300 for fixating soft tissue to bone is provided. This embodiment of the repair device system 300 may include structure and function similar to previous embodiments set forth herein. For example, the repair device system 300 may include a soft tissue anchor 302 and a bone anchor 304 that may be coupled together with a flexible member 306. The soft tissue anchor 302 and the flexible member 306 may be substantially similar to that described in the previous embodiment, except the flexible member 306 may extend longer alongside the bone anchor 304. Further, as depicted in FIGS. 14 and 14A, in this embodiment, the bone anchor 304 may include a hole 308 extending longitudinally along a length 310 of the bone anchor 304 between a proximal end 312 and a distal end 314 of the bone anchor 304. Such hole 308 defined in the bone anchor 304 may be sized and configured to receive a guidewire 316 associated with a delivery instrument 330 (see FIG. 16A) such that the guidewire 316 may pass completely through the bone anchor 304 and extend coaxially with a bone anchor axis 305. Further, the bone anchor 304 may define opposing first and second recesses 318, 320 in a distal portion 322 of the bone anchor 304 such that the first and second recesses 318, 320 may be positioned on opposite sides of the bone anchor 304. The first and second recesses 318, 320 may each extend with an upper downward extending lip 324 sized and configured to hold respective portions of the flexible member 306 within the first and second recesses 318, 320. The position of the first and second recesses 318, 320 may be off-set along the length 310 of the bone anchor 304 so as to extend laterally different distances relative to the distal end 314 of the bone anchor 304.

Figure 16:
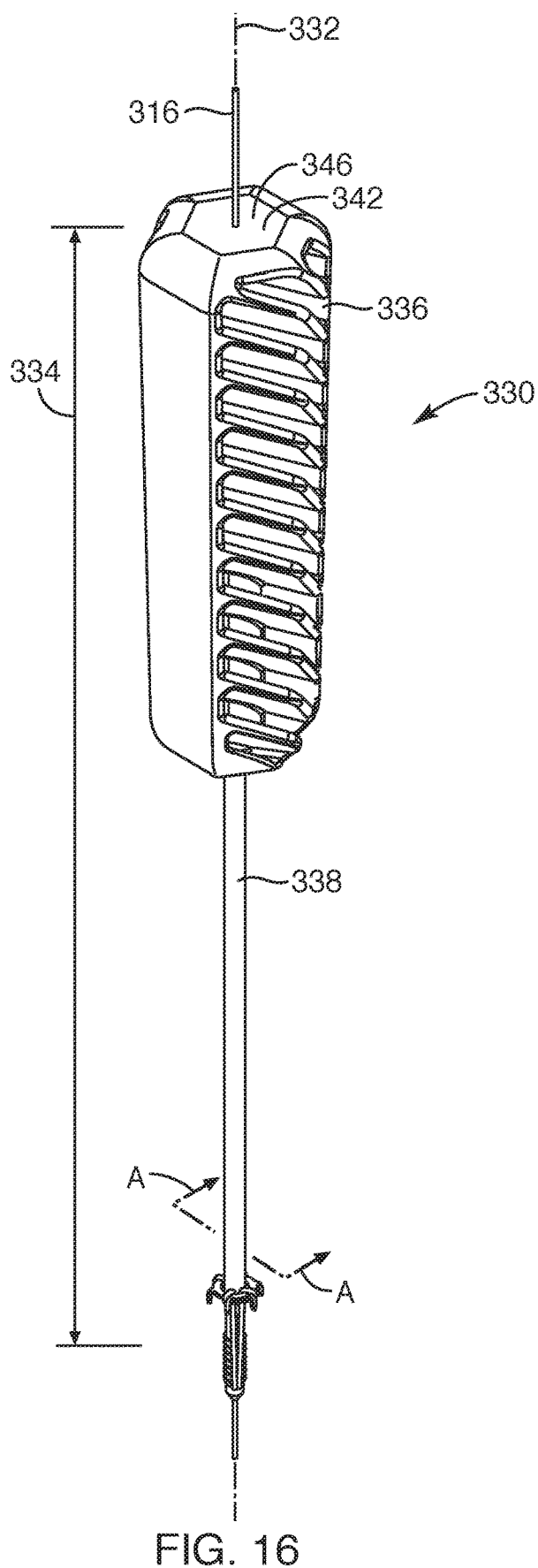
FIG. 16 is a perspective view of another embodiment of a medical device system, depicting a delivery instrument and guidewire employed for delivering the repair device system of FIG. 14, according to the present invention.
Figure 16A:
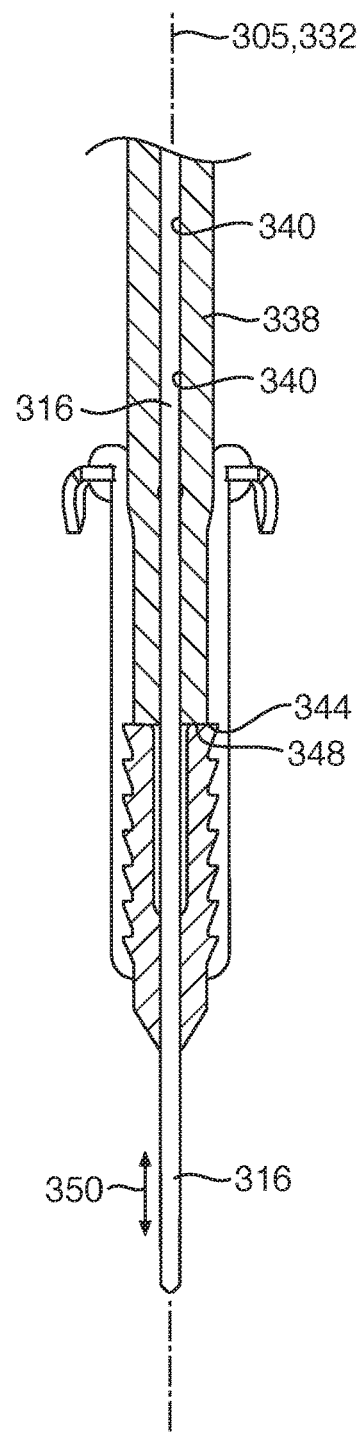
FIG. 16A is an enlarged cross-sectional view of a portion of the medical device system and repair device system taken along section line A-A of FIG. 16, according to the present invention.

Now with reference to FIGS. 16 and 16A, the repair device system 300 may be removably coupled to a delivery instrument 330. In this embodiment, the delivery instrument 330 may define a delivery instrument axis 332 extending longitudinally along a length 334 of the delivery instrument 330. The delivery instrument 330 may include a handle 336 and a shaft 338 such that the shaft 338 may be fixedly coupled to the handle 336 along the delivery instrument axis 332. The delivery instrument 330 may define a through hole 340 extending longitudinally through the handle 336 and the shaft 338 so as to extend completely through the delivery instrument 330 between a proximal end 342 and a distal end 344 thereof. Such through hole 340 may be sized and configured to receive the guidewire 316 therethrough so that the guidewire 316 may move bi-directionally in a distal and proximal direction, as shown by arrow 350. The proximal end 342 of the handle 336 may define a proximal impact surface 346 and the distal end 344 of the shaft 338 may define distal impact surface 348. The distal impact surface 348 may be sized and configured to abut with the proximal end 342 of the bone anchor 304 with the through hole 340 of the delivery instrument 330 axially aligned with the hole 308 of the bone anchor 304. Further, the delivery instrument 330 may be employed with the retainer element 274 (see FIG. 13A) to removably couple the repair device system 300 to the delivery instrument 330 and to place the flexible member 306 in a taut position so that the soft tissue anchor 302 is positioned a predetermined distance away from the bone anchor 304.

Figure 19:
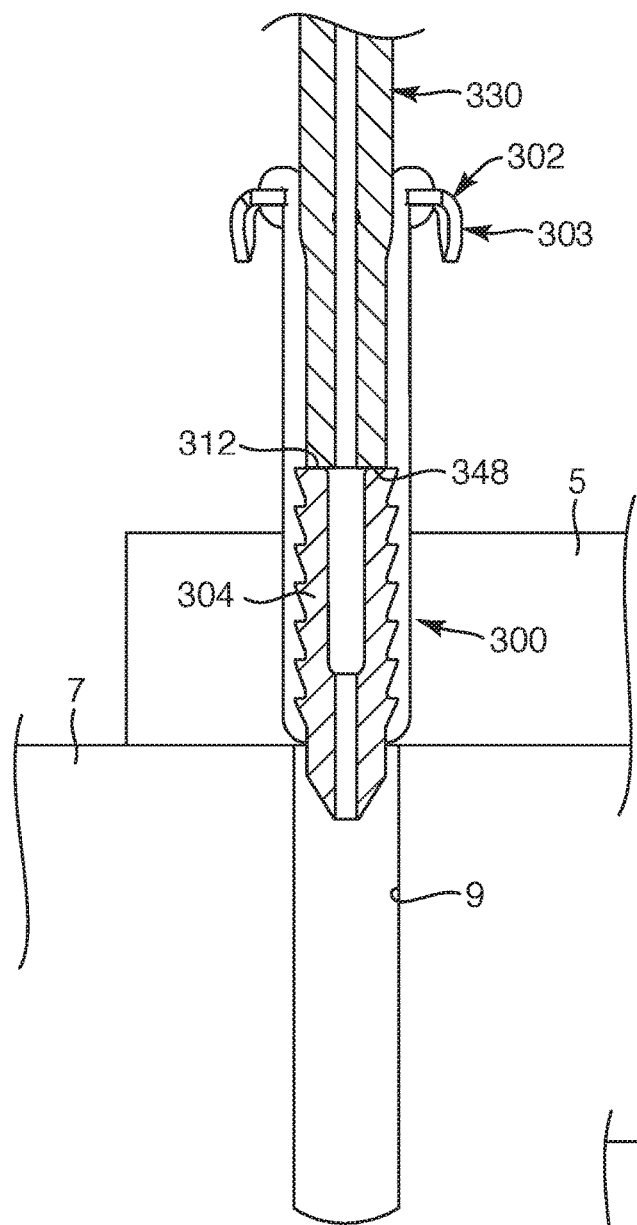
FIG. 19 is an enlarged cross-sectional view of the medical device system, depicting the guidewire removed from the pre-formed hole in the bone, according to another embodiment of the present invention.
Figure 20:
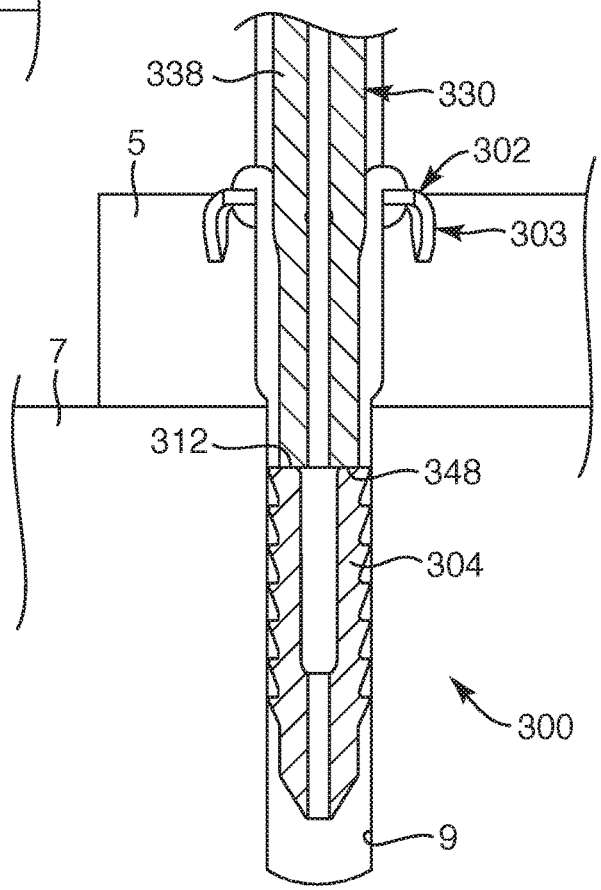
FIG. 20 is an enlarged cross-sectional view of the medical device system, depicting a delivery instrument subsequent to impacting the bone anchor into the pre-formed hole in the bone to fixate soft tissue to the bone, according to another embodiment of the present invention.
Figure 21:
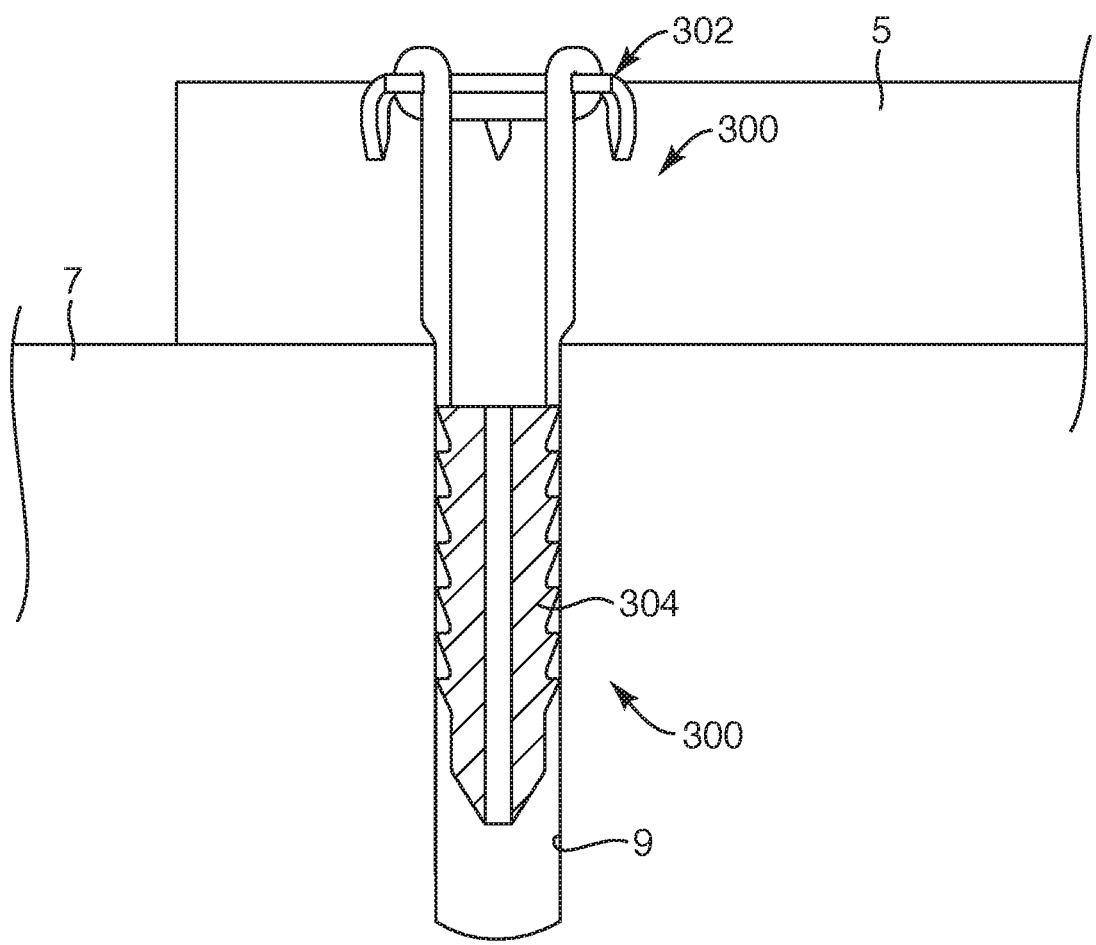
FIG. 21 is a cross-sectional view of the repair device system, depicting soft tissue fixated to bone with the repair device system, according to another embodiment of the present invention.

Now with reference to FIGS. 17-21, one embodiment for fixating soft tissue 5 to bone 7 with the repair device system 300 and the delivery instrument 330 is provided. For example, with respect to FIG. 17, a physician may prepare a repair site for soft tissue 5 to be fixated to bone 7. Such preparation may include forming a hole 9 in the bone 7. The physician may then position the soft tissue 5 over the previously formed hole 9 in the bone and prepare the positioned soft tissue 5 with a small slice therein. With reference to FIGS. 17 and 18, the physician may then move the guidewire 316 distally, as shown by arrow 360, to position the guidewire 316 through the small slice in the soft tissue 5 so that a distal end 362 of the guidewire 316 is positioned in the pre-formed hole 9 in the bone 7. The physician may then move the distal end 314 of the bone anchor 304 distally over the guidewire 316 so that a conical surface 364 of the bone anchor is pushed into the pre-formed hole 9, as shown in FIG. 18. At this stage, the physician may withdraw the guidewire 316 from the pre-formed hole 9 and from the repair device system 300 and the deliver instrument 330, as depicted in FIG. 19. With respect to FIGS. 19 and 20, the physician may then take a mallet or hammer like object (not shown) to impact the proximal end 342 of the handle 336 (FIG. 17), which results in the distal impact surface 348 of the delivery instrument 330 to impact the proximal end 312 of the bone anchor 304, thereby, forcing the bone anchor 304 further into the pre-formed hole 9. As the bone anchor 304 is forced into the pre-formed hole 9, the legs 303 of the soft tissue anchor 302 are simultaneously forced into the soft tissue 5, thereby, fixating the soft tissue 5 against the bone 7 in a clamping manner, as shown in FIG. 20. With respect to FIGS. 20 and 21, once the physician is satisfied with the depth of the bone anchor 304 within the pre-formed hole 9 and the clamping force of the soft tissue anchor 302 against the soft tissue 5, the physician may remove the delivery instrument 330 from the implanted repair device system 300. Similar to that depicted and described relative to FIGS. 13 and 13A, such removal of the delivery instrument 330 may be employed by removing the retainer element 274 by removing the tab 278 of the retainer element 274 from the shaft 338 of the delivery instrument 330. Once removed, the line extending under the soft tissue anchor may readily be withdrawn. In this manner, the delivery instrument 330 may be employed with the repair device system 300 for fixating soft tissue 5 to bone 7 at a soft tissue repair site.

The various repair device and system embodiments or other embodiments disclosed herein may be applied to any one of various soft tissue to bone repairs. For example, the various repair device embodiments may be employed for flexor tendon repairs, patellar tendon repairs, Achilles tendon repairs, quadriceps tendon repairs, and/or bicep tendon repairs, or any other tendon/ligament to bone repairs, such as kidner procedures or insertional Achilles repairs, or any other tendon/ligament to bone repairs. As such, the repair device may be appropriately sized for proper fixation to the different sized or types of soft tissue and bone.

While the invention may be susceptible to various modifications and alternative forms, specific embodiments have been shown by way of example in the drawings and have been described in detail herein. Further, the structural features of any one embodiment disclosed herein may be combined or replaced by any one of the structural features of another embodiment set forth herein. As such, it should be understood that the invention is not intended to be limited to the particular forms disclosed. Rather, the invention includes employing any portion of one embodiment with another embodiment, all modifications, equivalents, and alternatives, falling within the spirit and scope of the invention as defined by the following appended claims.

What is claimed is:
1. A medical device system for fixating soft tissue to bone, the medical device system comprising:
 a delivery instrument having an elongated portion defining a delivery instrument axis, the delivery instrument including a distal impacting surface and a proximal impacting surface, the delivery instrument including an alignment hole defined in the distal impacting surface and extending longitudinally along the delivery instrument axis; and a repair device system configured to be removably coupled to the delivery instrument, the repair device system including:
  a bone anchor having an elongated structure extending between a proximal end and a distal end, the bone anchor defining a bone anchor axis extending along the elongated structure, the bone anchor defining a hole therein extending between the proximal end and the distal end and along the bone anchor axis, the hole of the bone anchor configured to correspond with and be aligned with the alignment hole of the delivery instrument;
  a soft tissue anchor having a base with multiple legs extending from the base, the base defining a central opening defining a tissue anchor axis; and
  one or more flexible members extending to couple the soft tissue anchor to the bone anchor;
wherein the repair device system is removably coupled to the delivery instrument with the elongated portion extending through the central opening of the soft tissue anchor and the distal impacting surface abutted against the proximal end of the bone anchor such that, as the bone anchor is being implanted into bone, the one or more flexible members extend taut between the bone anchor and the soft tissue anchor to simultaneously pull the soft tissue anchor into the soft tissue.

2. The medical device system of claim 1, further comprising a guidewire configured to assist in delivering the repair device system with the delivery instrument, the guidewire sized and configured to be bi-linearly moveable within and through the alignment hole of the delivery instrument and the hole of the bone anchor.

3. The repair device system of claim 1, wherein the bone anchor defines a first side notch and a second side notch positioned adjacent a distal end portion of the bone anchor, the first and second side notches being positioned along opposite sides of the bone anchor and sized and configured to hold the one or more flexible members to the bone anchor.

4. The repair device system of claim 3, wherein the first side notch and the second side notch are positioned along the opposite sides of the bone anchor in an off-set manner relative to and along the bone anchor axis.

5. The medical device system of claim 1, wherein the repair device system is configured to be delivered with the delivery instrument such that the delivery instrument axis is substantially coaxial, or substantially parallel, with the bone anchor axis and the tissue anchor axis.

6. The medical device system of claim 1, wherein the one or more flexible members are a fixed length such that, upon the one or more flexible members being in a taut position, the one or more flexible members maintain a substantially fixed distance between the bone anchor and the soft tissue anchor in a pre-delivered state and a delivered state.

7. The medical device system of claim 1, further comprising a retainer element having a line positioned along an underside of the soft tissue anchor to position the one or more flexible members in a taut position and removably couple the repair device system to the delivery instrument.

8. A medical device system for fixating soft tissue to bone, the medical device system comprising:
  a delivery instrument having an elongated portion defining a delivery instrument axis, the delivery instrument including a distal impacting surface and a proximal impacting surface, the delivery instrument including alignment structure defined along the distal impacting surface and extending longitudinally with the delivery instrument axis; and
  a repair device system configured to be removably coupled to the delivery instrument, the repair device system including:
    a bone anchor having an elongated structure extending between a proximal end and a distal end, the bone anchor defining a bone anchor axis extending along the elongated structure, the bone anchor defining a hole therein extending between the proximal end and the distal end and along the bone anchor axis, the hole of the bone anchor configured to correspond with and be aligned with the alignment structure of the delivery instrument;
    a soft tissue anchor having a base with multiple legs extending from the base, the base defining a central opening defining a tissue anchor axis; and
    one or more flexible members extending to couple the soft tissue anchor to the bone anchor;
  wherein the repair device system is removably coupled to the delivery instrument with the elongated portion extending through the central opening of the soft tissue anchor and the distal impacting surface abutted against the proximal end of the bone anchor such that, upon the bone anchor being implanted into the bone, the one or more flexible members extend taut between the bone anchor and the soft tissue anchor to simultaneously pull the soft tissue anchor into the soft tissue.

9. The medical device system of claim 8, further comprising a guidewire configured to assist in delivering the repair device system with the delivery instrument, the guidewire sized and configured to be bi-linearly moveable within and through an instrument hole of the alignment structure of the delivery instrument and the hole of the bone anchor.

10. The repair device system of claim 8, wherein the bone anchor defines a first side notch and a second side notch positioned adjacent a distal end portion of the bone anchor, the first and second side notches being positioned along opposite sides of the bone anchor and sized and configured to hold the one or more flexible members to the bone anchor.

11. The repair device system of claim 10, wherein the first side notch and the second side notch are positioned along the opposite sides of the bone anchor in an off-set manner relative to and along the bone anchor axis.

12. The medical device system of claim 8, wherein the repair device system is configured to be delivered with the delivery instrument such that the delivery instrument axis is substantially coaxial, or substantially parallel, with the bone anchor axis and the tissue anchor axis.

13. The medical device system of claim 8, wherein the one or more flexible members are a fixed length such that, upon the one or more flexible members being in a taut position, the one or more flexible members maintain a substantially fixed distance between the bone anchor and the soft tissue anchor in a pre-delivered state and a delivered state.

14. The medical device system of claim 8, further comprising a retainer element having a line positioned along an underside of the soft tissue anchor to position the one or more flexible members in a taut position and removably couple the repair device system to the delivery instrument.

* * * * *